(12) United States Patent
Bally et al.

(10) Patent No.: US 10,959,805 B1
(45) Date of Patent: Mar. 30, 2021

(54) TRANSFER DEVICE DOCKING INDICATOR

(71) Applicant: Nexxspan Healthcare, LLC, Norcross, GA (US)

(72) Inventors: Alexander Bally, Marston Mills, MA (US); Eric Richard Colburn, Pittsburgh, PA (US)

(73) Assignee: Nexxspan Healthcare, LLC, Norcross, GA (US)

( * ) Notice: Subject to any disclaimer, the term of this patent is extended or adjusted under 35 U.S.C. 154(b) by 0 days.

(21) Appl. No.: 17/065,288

(22) Filed: Oct. 7, 2020

Related U.S. Application Data

(60) Provisional application No. 62/912,371, filed on Oct. 8, 2019.

(51) Int. Cl.
*F16M 13/02* (2006.01)
*A61G 7/05* (2006.01)
(Continued)

(52) U.S. Cl.
CPC .............. *A61B 90/90* (2016.02); *A61B 50/20* (2016.02); *A61G 7/012* (2013.01); *A61G 7/0503* (2013.01);
(Continued)

(58) Field of Classification Search
CPC . A61G 7/01; A61G 7/012; A61G 7/05; A61G 7/0503; A61G 7/10; A61B 50/20; A61B 90/90; A61M 5/14; A61M 5/1417; A61M 2205/6036; F16M 11/08; F16M 11/18; F16M 13/00; F16M 13/02; F16M 13/022
USPC .... 248/205.1, 127, 128, 129, 518, 519, 521, 248/274.1, 276.1, 158, 159; 5/503.1, 5/507.1, 600, 658; 403/12, 325, 326, 334
See application file for complete search history.

(56) References Cited

U.S. PATENT DOCUMENTS 2,085,074 A 6/1937 Boyles
2,409,432 A 10/1946 Hubbard
(Continued)

FOREIGN PATENT DOCUMENTS

AU 2013404103 2/2018
CA 2925543 12/2020
(Continued)

OTHER PUBLICATIONS

Bally, Alexander; Issue Notification for U.S. Appl. No. 13/104,531, filed May 10, 2011, mailed Oct. 23, 2013, 1 pg.
(Continued)

*Primary Examiner* — Scott A Smith
(74) *Attorney, Agent, or Firm* — Taylor English Duma LLP

(57) ABSTRACT

A transfer system can include a receiver; and a transfer device including: a housing comprising a first docking cup and a second docking cup, each of the first docking cup and the second docking cup configured to receive and lockably engage the receiver; a security mechanism positioned inside the housing and configured to engage with the receiver through either of the first docking cup and the second docking cup; and a pair of indicators coupled to the security mechanism and at least partially visible from outside the housing, each of the pair of indicators configured to indicate to a user of the transfer system that the receiver has been lockably engaged with one of the first docking cup and the second docking cup.

20 Claims, 26 Drawing Sheets

(51) Int. Cl.
*A61B 90/90* (2016.01)
*A61B 50/20* (2016.01)
*A61G 7/012* (2006.01)
*A61G 7/10* (2006.01)
*F16M 13/00* (2006.01)
*A61M 5/14* (2006.01)
*F16M 11/18* (2006.01)
*F16M 11/08* (2006.01)

(52) U.S. Cl.
CPC ............. *A61G 7/10* (2013.01); *F16M 13/00* (2013.01); *A61G 7/05* (2013.01); *A61M 5/1417* (2013.01); *A61M 2205/6036* (2013.01); *F16M 11/08* (2013.01); *F16M 11/18* (2013.01); *F16M 13/02* (2013.01); *F16M 13/022* (2013.01)

(56) References Cited

U.S. PATENT DOCUMENTS

| | | | |
|---|---|---|---|
| 2,460,244 A | 1/1949 | Strauss | |
| 3,570,376 A | 3/1971 | Overton | |
| 3,912,405 A | 10/1975 | Katt | |
| 4,214,685 A | 7/1980 | Pletz | |
| D262,237 S | 12/1981 | Stauber | |
| 4,367,871 A | 1/1983 | Schiefer | |
| 4,511,158 A | 4/1985 | Varga et al. | |
| 4,725,027 A | 2/1988 | Bekanich | |
| 4,869,552 A | 9/1989 | Tolleson et al. | |
| 4,945,592 A | 8/1990 | Sims et al. | |
| 5,160,111 A | 11/1992 | Hugron | |
| D339,195 S | 9/1993 | Nash et al. | |
| 5,306,109 A | 4/1994 | Kreuzer et al. | |
| 5,366,191 A | 11/1994 | Bekanich | |
| 5,474,408 A | 12/1995 | Dinitz | |
| 5,527,125 A * | 6/1996 | Kreuzer | A61G 12/00 248/316.3 |
| 5,618,090 A * | 4/1997 | Montague | A61G 12/002 312/209 |
| D381,745 S | 7/1997 | Owens | |
| 5,797,613 A | 8/1998 | Busby | |
| 5,865,456 A | 2/1999 | Busby et al. | |
| 5,898,961 A * | 5/1999 | Ambach | A61G 7/05 292/108 |
| 6,042,292 A | 3/2000 | Belanger | |
| 6,073,285 A * | 6/2000 | Ambach | A61G 7/05 292/252 |
| 6,308,927 B1 | 10/2001 | Leahy | |
| 6,516,573 B1 | 2/2003 | Farrell et al. | |
| 7,008,269 B2 * | 3/2006 | Riley | A61G 7/05 439/668 |
| 7,065,812 B2 * | 6/2006 | Newkirk | A61G 7/0503 248/125.8 |
| 7,219,472 B2 * | 5/2007 | Gallant | E04B 2/745 52/36.2 |
| 7,254,850 B2 | 8/2007 | Newkirk et al. | |
| 7,258,310 B2 | 8/2007 | Norris | |
| 7,314,200 B2 | 1/2008 | Bally | |
| 7,418,749 B2 | 9/2008 | Graham et al. | |
| 7,624,463 B2 * | 12/2009 | Graham | A61G 7/0503 5/600 |
| 7,661,641 B2 * | 2/2010 | Wong | A61G 13/107 248/274.1 |
| 7,676,865 B2 | 3/2010 | Graham et al. | |
| 7,735,788 B2 | 6/2010 | Newkirk et al. | |
| 7,748,672 B2 | 7/2010 | Walke | |
| 7,770,247 B2 * | 8/2010 | Lubbers | F16D 63/008 5/600 |
| 7,789,361 B2 * | 9/2010 | Bally | F16M 11/041 248/229.2 |
| 7,798,456 B2 | 9/2010 | Newkirk et al. | |
| 7,845,601 B1 * | 12/2010 | Culpepper | A61M 5/1418 248/125.2 |
| 7,865,983 B2 | 1/2011 | Newkirk et al. | |
| 7,980,533 B1 | 7/2011 | Anderson | |
| 8,104,729 B2 | 1/2012 | Walke et al. | |
| D655,408 S | 3/2012 | Bally | |
| D655,409 S | 3/2012 | Bally | |
| 8,403,275 B2 * | 3/2013 | Cote | A61M 5/1415 248/129 |
| 8,579,244 B2 * | 11/2013 | Bally | A61G 12/005 248/276.1 |
| 9,404,616 B2 * | 8/2016 | Bally | A61M 5/1417 |
| 9,528,536 B2 * | 12/2016 | Bally | F16M 11/42 |
| 9,816,663 B2 * | 11/2017 | Bally | F16M 13/02 |
| 9,827,062 B2 * | 11/2017 | Bally | A61M 5/1417 |
| 10,258,424 B2 | 4/2019 | Bally | |
| 10,258,524 B2 | 4/2019 | Bally | |
| 2004/0164220 A1 * | 8/2004 | Newkirk | A61B 50/10 248/647 |
| 2005/0253034 A1 | 11/2005 | Bally et al. | |
| 2006/0179571 A1 * | 8/2006 | Newkirk | A61G 12/004 5/600 |
| 2006/0242763 A1 * | 11/2006 | Graham | A61G 12/004 5/503.1 |
| 2006/0249641 A1 | 11/2006 | Bally et al. | |
| 2007/0069093 A1 | 3/2007 | Graham et al. | |
| 2007/0157385 A1 | 7/2007 | Lemire et al. | |
| 2007/0267550 A1 | 11/2007 | Blankenship et al. | |
| 2008/0149788 A1 | 6/2008 | Wong et al. | |
| 2008/0217910 A1 * | 9/2008 | Welke | A61G 12/002 285/121.7 |
| 2009/0050756 A1 | 2/2009 | Newkirk et al. | |
| 2009/0065668 A1 | 3/2009 | Walke | |
| 2011/0217876 A1 | 9/2011 | Siebens | |
| 2011/0272538 A1 * | 11/2011 | Bally | A61G 12/005 248/205.1 |
| 2013/0125367 A1 | 5/2013 | Rode | |
| 2014/0048661 A1 | 2/2014 | Bally | |
| 2014/0237721 A1 | 8/2014 | Lemire et al. | |
| 2015/0216606 A1 | 8/2015 | Bally | |
| 2016/0153611 A1 | 6/2016 | Bally | |
| 2017/0049525 A1 | 2/2017 | Bally | |
| 2017/0241457 A1 | 8/2017 | Bally | |
| 2017/0241461 A1 | 8/2017 | Bally | |

FOREIGN PATENT DOCUMENTS

| | | |
|---|---|---|
| EP | 3063454 | 9/2018 |
| FR | 2914329 | 10/2008 |
| NL | 2000571 | 10/2008 |
| WO | 2015065309 | 5/2015 |
| WO | 2016167817 | 10/2016 |
| WO | 2017147005 | 8/2017 |

OTHER PUBLICATIONS

Bally, Alexander; Non-Final Office Action for U.S. Appl. No. 13/104,531, filed May 10, 2011, dated Apr. 23, 2013, 15 pgs.
Bally, Alexander; Notice of Allowance for U.S. Appl. No. 13/104,531, filed May 10, 2011, dated Aug. 22, 2013, 12 pgs.
Bally, Alexander; Restriction Requirement for U.S. Appl. No. 13/104,531, filed May 10, 2011, dated Feb. 5, 2013, 6 pgs.
Bally, Alexander; Final Office Action for U.S. Appl. No. 14/064,345, filed Oct. 28, 2013, dated Jul. 15, 2015, 9 pgs.
Bally, Alexander; Issue Notification for U.S. Appl. No. 14/064,345, filed Oct. 28, 2013, dated Feb. 24, 2016, 1 pg.
Bally, Alexander; Issue Notification for U.S. Appl. No. 14/064,345, filed Oct. 28, 2013, dated Jul. 13, 2016, 1 pg.
Bally, Alexander; Non-Final Office Action for U.S. Appl. No. 14/064,345, filed Oct. 28, 2013, dated Apr. 6, 2015, 14 pgs.
Bally, Alexander; Notice of Allowance for U.S. Appl. No. 14/064,345, filed Oct. 28, 2013, dated Nov. 9, 2015, 10 pgs.
Bally, Alexander; Notice of Allowance for U.S. Appl. No. 14/064,345, filed Oct. 28, 2013, dated Mar. 25, 2016, 10 pgs.
Bally, Alexander; Advisory Action for U.S. Appl. No. 14/686,439, filed Apr. 14, 2015, dated Jul. 11, 2016, 3 pgs.
Bally, Alexander; Applicant Initiated Interview Summary for U.S. Appl. No. 14/686,439, filed Apr. 14, 2015, dated Jun. 17, 2016, 3 pgs.

(56) References Cited

OTHER PUBLICATIONS

Bally, Alexander; Applicant-Initiated Interview Summary for U.S. Appl. No. 14/686,439, filed Apr. 14, 2015, dated Oct. 22, 2015, 3 pgs.
Bally, Alexander; Final Office Action for U.S. Patent Application No. 14/686,439, filed Apr. 14, 2015, dated Mar. 31, 2016, 14 pgs.
Bally, Alexander; Issue Notification for U.S. Appl. No. 14/686,439, filed Apr. 14, 2015, dated Dec. 8, 2016, 1 pg.
Bally, Alexander; Non-Final Office Action for U.S. Appl. No. 14/686,439, filed Apr. 14, 2015, dated Sep. 1, 2015, 20 pgs.
Bally, Alexander; Notice of Allowance for U.S. Appl. No. 14/686,439, filed Apr. 14, 2015, dated Aug. 15, 2016, 12 pgs.
Bally, Alexander; Applicant Initiated Interview Summary for U.S. Appl. No. 15/019,323, filed Feb. 9, 2016, dated Dec. 20, 2016, 3 pgs.
Bally, Alexander; Final Office Action for U.S. Appl. No. 15/019,323, filed Feb. 9, 2016, dated Apr. 26, 2017, 18 pgs.
Bally, Alexander; Issue Notification for U.S. Appl. No. 15/019,323, filed Feb. 9, 2016, dated Oct. 25, 2017, 1 pg.
Bally, Alexander; Non-Final Office Action for U.S. Appl. No. 15/019,323, filed Feb. 9, 2016, dated Oct. 18, 2016; 21 pgs.
Bally, Alexander; Notice of Allowance for U.S. Appl. No. 15/019,323, filed Feb. 9, 2016, dated Jul. 7, 2017, 12 pgs.
Bally, Alexander; Non-Final Office Action for U.S. Appl. No. 15/347,070, filed Nov. 9, 2016, dated Jan. 12, 2017; 17 pgs.
Bally, Alexander; Notice of Allowance for U.S. Appl. No. 15/347,070, filed Nov. 9, 2016, dated Jul. 27, 2017, 17 pgs.
Bally, Alexander; Final Office Action for U.S. Appl. No. 15/049,466, filed Feb. 22, 2016, dated Sep. 6, 2018, 20 pgs.
Bally, Alexander; Issue Notification for U.S. Appl. No. 15/049,466, filed Feb. 22, 2016, dated Mar. 27, 2019, 1 pg.
Bally, Alexander; Issue Notification for U.S. Appl. No. 15/347,070, filed Nov. 9, 2016, dated Nov. 8, 2017, 1 pg.
Bally, Alexander; Non-Final Office Action for U.S. Appl. No. 15/049,466, filed Feb. 22, 2016, dated Apr. 30, 2018, 53 pgs.
Bally, Alexander; Notice of Allowance for U.S. Appl. No. 15/049,466, filed Feb. 22, 2016, dated Jan. 7, 2019, 19 pgs.
Bally, Alexander; Invitation to Pay Additional Fees for PCT Application No. PCT/US17/18300, filed Feb. 17, 2017, dated May 3, 2017, 3 pgs.
Bally, Alexander; Applicant-Initiated Interview Summary for U.S. Appl No. 15/049,477, filed Feb. 22, 2016, dated Oct. 15, 2018, 3 pgs.
Bally, Alexander; Issue Notification for U.S. Appl. No. 15/049,477, filed Feb. 22, 2016, dated Mar. 27, 2019, 1 pg.
Bally, Alexander; Non-Final Office Action for U.S. Appl. No. 15/049,477, filed Feb. 22, 2016, dated Aug. 27, 2018, 57 pgs.
Bally, Alexander; Notice of Allowance for U.S. Appl. No. 15/049,477, filed Feb. 22, 2016, dated Dec. 4, 2018, 16 pgs.
Bally, Alexander; Requirement for Restriction/Election for U.S. Appl. No. 15/049,477, filed Feb. 22, 2016, dated May 14, 2018, 6 pgs.
Bally, Alexander; Supplemental Notice of Allowance for U.S. Appl. No. 15/049,477, filed Feb. 22, 2016, dated Dec. 28, 2018, 6 pgs.
Bally, Alexander; Supplemental Notice of Allowance for U.S. Appl. No. 15/049,477, filed Feb. 22, 2016, dated Mar. 6, 2019, 6 pgs.

Bally, Alexander; International Search Report and Written Opinion for PCT Application No. PCT/US17/18300, filed Feb. 17, 2017, dated Jun. 26, 2017, 14 pgs.
Bally, Alex; International Preliminary Report on Patentability for PCT/US2013/067007, filed Oct. 28, 2013, dated May 3, 2016, 6 pgs.
Bally, Alex; International Search Report and Written Opinion for PCT/US2013/067007, filed Oct. 28, 2013, dated Mar. 10, 2014, 8 pgs.
Bally, Alex; International Preliminary Report on Patentability for PCT Application No. PCT/US15/27300, filed Jan. 23, 2015, dated Oct. 26, 2017, 10 pgs.
Bally, Alex; International Search Report and Written Opinion for PCT Application No. PCT/US15/27300, filed Apr. 23, 2015, dated Sep. 1, 2015, 13 pgs.
Bally, Alex; First Examination Report for Australia U.S. Appl. No. 2013404103, filed Oct. 28, 2013, dated Jun. 9, 2017, 3 pages.
Bally, Alex; Office Action for Canadian patent application No. 2,925,543, filed Oct. 28, 2013, dated Aug. 6, 2019, 3 pgs.
Bally, Alex; Extended European Search Report for serial No. 13896274.1, filed Oct. 28, 2013, dated Apr. 24, 2017, 6 pgs.
Bally, Alex; Examination Report for Australian patent application No. 2015391040, filed Apr. 23, 2015, dated Feb. 6, 2020, 3 pgs.
Bally, Alex; European Search Report for serial No. 15889408.9, filed Apr. 23, 2015, dated Feb. 22, 2019, 10 pgs.
Bally, Alex; Office Action for European serial No. 15889408.9, filed Apr. 23, 2015, dated Nov. 5, 2019, 6 pgs.
Bally, Alex; Office Action for European serial No. 15889408.9, filed Apr. 23, 2015, dated Apr. 29, 2020, 5 pgs.
Bally, Alex; Partial European Search Report for serial No. 15889408.9, filed Apr. 23, 2015, dated Oct. 25, 2018, 11 pgs.
Bally, Alexander; International Preliminary Report on Patentability for PCT Application No. PCT/US17/18300, filed Feb. 17, 2017, dated Sep. 7, 2018, 11 pgs.
Bally, Alexander; Extended European Search Report for serial No. 17757029.8, filed Feb. 17, 2017, dated Mar. 24, 2020, 8 pgs.
Bally, Alexander; Non-Final Office Action for U.S. Appl. No. 29/393,210, filed Jun. 1, 2011, dated Oct. 26, 2011, 7 pgs.
Bally, Alexander; Notice of Allowance for U.S. Appl. No. 29/393,210, filed Jun. 1, 2011, dated Nov. 23, 2011, 5 pgs.
Bally, Alexander; Issue Notification for U.S. Appl. No. 29/393,210, filed Jun. 1, 2011, dated Feb. 15, 2012, 1 pg.
Bally, Alexander; Non-Final Office Action for U.S. Appl. No. 29/393,211, filed Jun. 1, 2011, dated Oct. 25, 2011, 6 pgs.
Bally, Alexander; Notice of Allowance for U.S. Appl. No. 29/393,211, filed Jun. 1, 2011, dated Nov. 25, 2011, 5 pgs.
Bally, Alexander; Issue Notification for U.S. Appl. No. 29/393,211, filed Jun. 1, 2011, dated Feb. 15, 2012, 1 pg.
IMEC-TRUMPF North America, article located at <www.us.trumpf.com/products/,,,/imec.html>, accessed on Sep. 1, 2010, 1 pg.
Bally, Alex; Summons to Attend Oral Proceedings for European serial No. 15889408.9, filed Apr. 23, 2015, mailed Dec. 4, 2020, 6 pgs.
Bally, Alexander; International Search Report and Written Opinion for PCT Application No. PCT/US20/54573, filed Oct. 7, 2020, dated Jan. 8, 2021, 8 pgs.

* cited by examiner

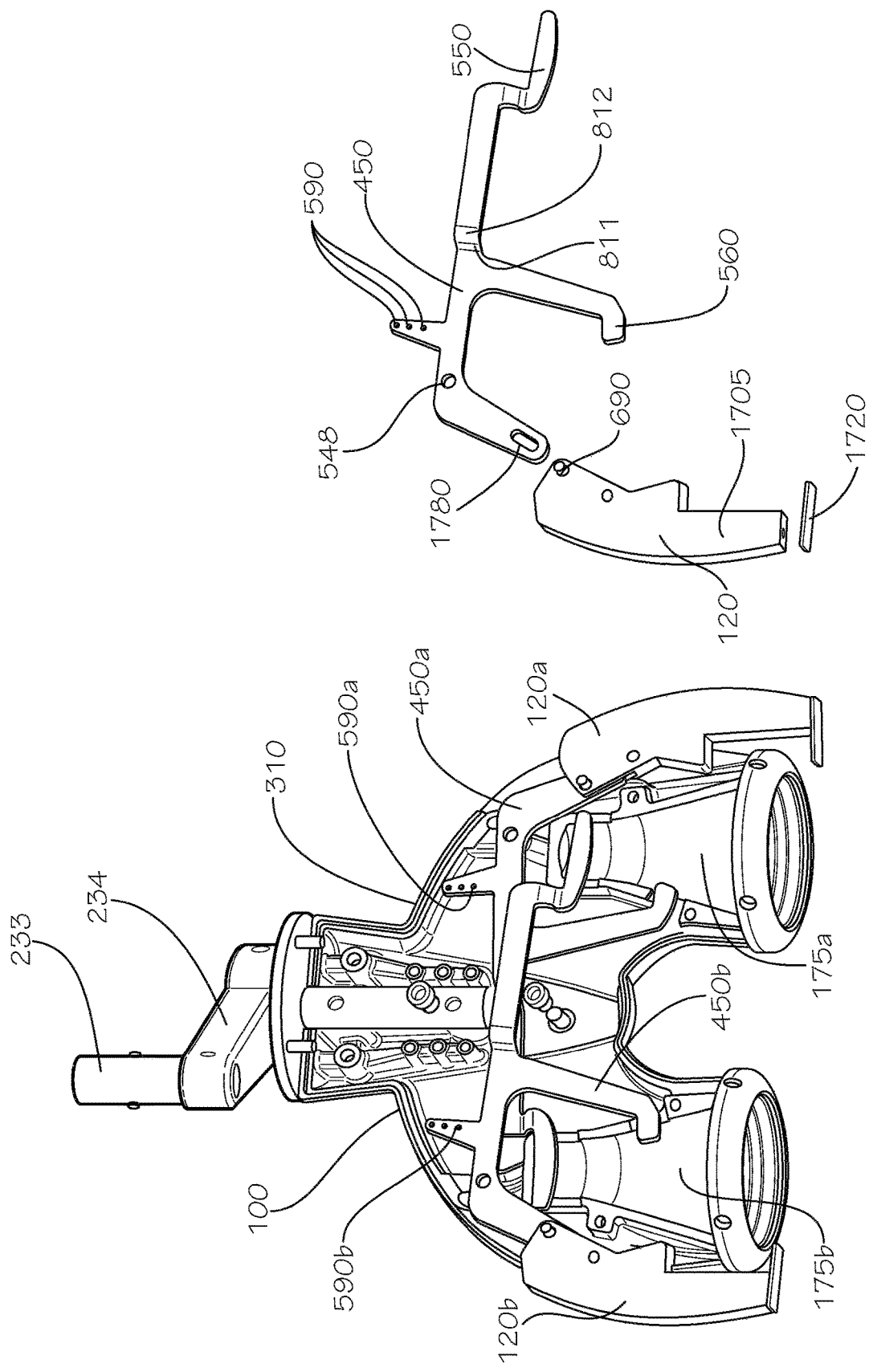

TRANSFER DEVICE DOCKING INDICATOR

REFERENCE TO RELATED APPLICATIONS

This application claims the benefit of U.S. Provisional Application No. 62/912,371, filed Oct. 8, 2019, which is hereby specifically incorporated by reference herein in its entirety.

TECHNICAL FIELD

Field of Use

This disclosure relates to transfer systems such as those used in a patient care environment. More specifically, this disclosure relates to transfer devices indicating a condition of engagement of disengagement with a support platform.

Related Art

In the care of medical patients, various medical equipment such as, for example and without limitation, infusion management equipment and supplies, pressure transducers, physiological monitors, and other equipment can be employed. Such equipment can be set up at the patient's bedside, where it can be supported by various stands, racks or hangers. For example, the equipment may be supported by 5-star floor stands, headwalls, booms such as those affixed to a ceiling, floor or wall mounted columns, or on other stationary or mobile platforms.

Such patients can at times be transported between rooms or facilities to facilitate their care. Such transports can often be necessary under emergency conditions while patients are distressed and frail, and for this reason and others it can be beneficial to complete such transports rapidly and with minimal disruption of therapy, life support, and monitoring.

In addition to moving the patient bed, caregivers must typically also wheel several intravenous-fluid (IV) stands next to or behind a bed, or pile the equipment onto the mattress next to the patient. These techniques can prove hazardous because the IV stands may fall and tear out patient connections. Such patient transports can also be inefficient and costly because significant staff time is required to prepare a patient for transport and many caregivers are needed for moving the equipment in tandem with the bed along corridors, into and out of elevators, and through doors.

Some transfer systems exist for supporting and transferring equipment from one support platform to another to facilitate transport of patients, but it is not always clear to caregivers during use of the transfer systems when the equipment and specifically a transfer device of the transfer system supporting the equipment is positively locked in place and ready for transport. In some conditions, including when the components of the transfer system are not properly aligned, docking of one component with another may not occur as expected.

SUMMARY

It is to be understood that this summary is not an extensive overview of the disclosure. This summary is exemplary and not restrictive, and it is intended to neither identify key or critical elements of the disclosure nor delineate the scope thereof. The sole purpose of this summary is to explain and exemplify certain concepts of the disclosure as an introduction to the following complete and extensive detailed description.

In one aspect, disclosed is a transfer system comprising: a receiver; and a transfer device comprising: a housing comprising a first docking cup and a second docking cup, each of the first docking cup and the second docking cup configured to receive and lockably engage the receiver; a security mechanism positioned inside the housing and configured to engage with the receiver through either of the first docking cup and the second docking cup; and a pair of indicators coupled to the security mechanism and at least partially visible from outside the housing, each of the pair of indicators configured to indicate to a user of the transfer system that the receiver has been lockably engaged with one of the first docking cup and the second docking cup.

In a further aspect, disclosed is a transfer device comprising: a housing comprising a first docking cup and a second docking cup, each of the first docking cup and the second docking cup configured to receive and lockably engage a receiver of a transfer system; a security mechanism positioned inside the housing; and a pair of indicators coupled to the security mechanism and at least partially visible from outside the housing, each of the pair of indicators configured to indicate to a user of the transfer system that the receiver has been lockably engaged with one of the first docking cup and the second docking cup.

In yet another aspect, disclosed is a method of using a transfer system, the method comprising: lockably engaging a transfer device of the transfer system with a receiver of the transfer system, the transfer device comprising: a housing comprising a first docking cup and a second docking cup, lockably engaging the transfer device comprising lockably engaging the receiver with one of the first docking cup and the second docking cup; a security mechanism positioned inside the housing; and a pair of indicators coupled to the security mechanism and at least partially visible from outside the housing; and positioning a first indicator of the pair of indicators in a first indicating position with respect to the housing, the first indicating position indicating to a user of the transfer system that the receiver has been lockably engaged with the one of the first docking cup and the second docking cup.

Various implementations described in the present disclosure may comprise additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims. The features and advantages of such implementations may be realized and obtained by means of the systems, methods, features particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

The accompanying drawings, which are incorporated in and constitute a part of this specification, illustrate several aspects of the disclosure and together with the description, serve to explain various principles of the disclosure. The drawings are not necessarily drawn to scale. Corresponding features and components throughout the figures may be designated by matching reference characters for the sake of consistency and clarity.

FIG. 17D is a front perspective view of the transfer device of FIG. 17A with at least a portion of the housing of the transfer device removed.

FIG. 17E is a front exploded perspective view of an indicator and a security lever of a security mechanism of the transfer device of FIG. 17A.

DETAILED DESCRIPTION

Figure 1:
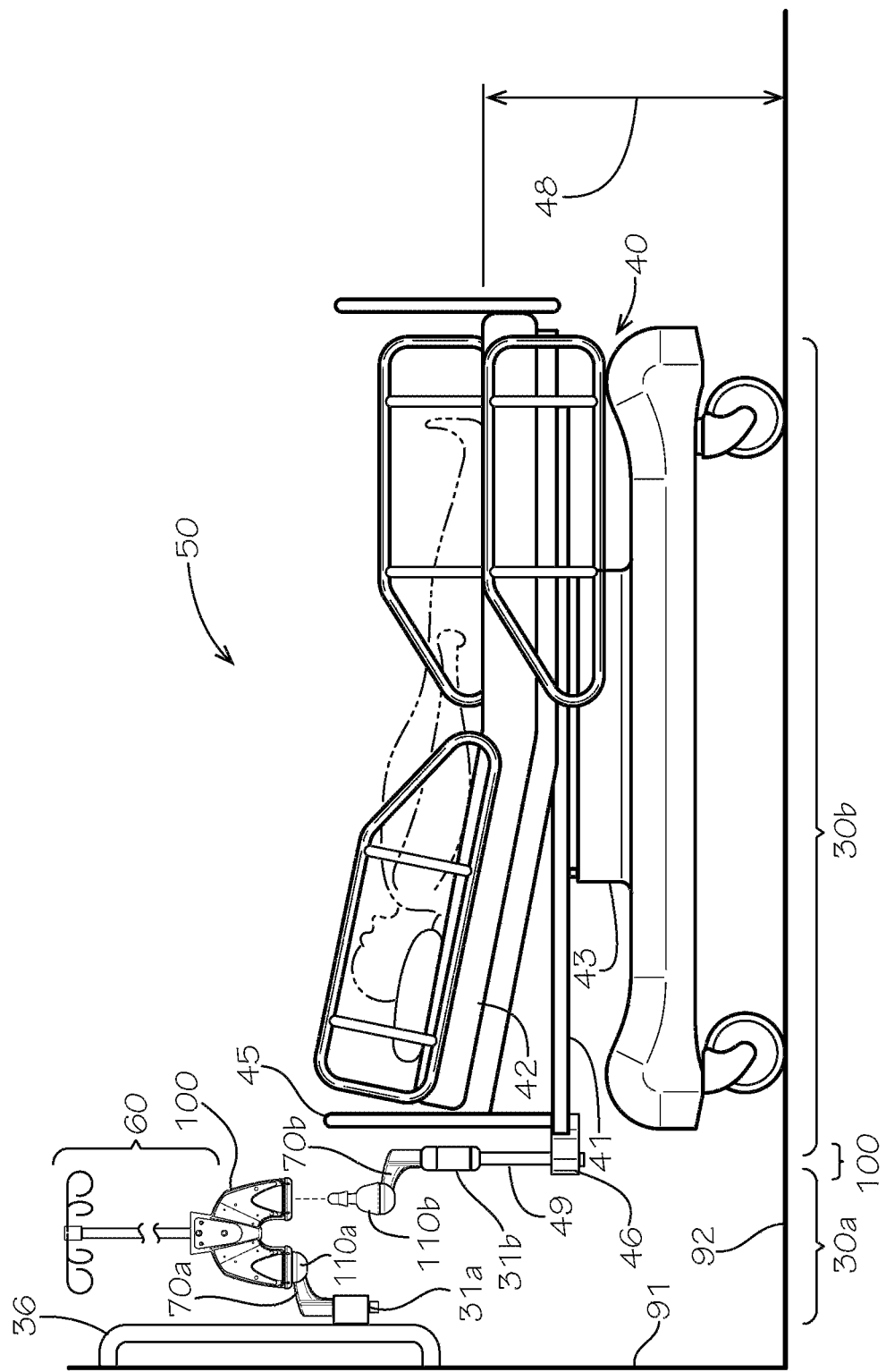
FIG. 1 is a side view of a transfer system in a medical environment, the transfer system comprising a stationary support platform, a mobile support platform, and a transfer device supporting a patient care apparatus in accordance with one aspect of the current disclosure, the transfer device comprising a set of indicators.

The present disclosure can be understood more readily by reference to the following detailed description, examples, drawings, and claims, and their previous and following description. However, before the present devices, systems, and/or methods are disclosed and described, it is to be understood that this disclosure is not limited to the specific devices, systems, and/or methods disclosed unless otherwise specified, as such can, of course, vary. It is also to be understood that the terminology used herein is for the purpose of describing particular aspects only and is not intended to be limiting.

The following description is provided as an enabling teaching of the present devices, systems, and/or methods in their best, currently known aspect. To this end, those skilled in the relevant art will recognize and appreciate that many changes can be made to the various aspects described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

As used throughout, the singular forms "a," "an" and "the" include plural referents unless the context clearly dictates otherwise. Thus, for example, reference to a quantity of one of a particular element can comprise two or more such elements unless the context indicates otherwise. In addition, any of the elements described herein can be a first such element, a second such element, and so forth (e.g., a first widget and a second widget, even if only a "widget" is referenced).

Ranges can be expressed herein as from "about" one particular value, and/or to "about" another particular value. When such a range is expressed, another aspect comprises from the one particular value and/or to the other particular value. Similarly, when values are expressed as approximations, by use of the antecedent "about" or "substantially," it will be understood that the particular value forms another aspect. It will be further understood that the endpoints of each of the ranges are significant both in relation to the other endpoint, and independently of the other endpoint.

For purposes of the current disclosure, a material property or dimension measuring about X or substantially X on a particular measurement scale measures within a range between X plus an industry-standard upper tolerance for the specified measurement and X minus an industry-standard lower tolerance for the specified measurement. Because tolerances can vary between different materials, processes and between different models, the tolerance for a particular measurement of a particular component can fall within a range of tolerances.

As used herein, the terms "optional" or "optionally" mean that the subsequently described event or circumstance may or may not occur, and that the description comprises instances where said event or circumstance occurs and instances where it does not.

The word "or" as used herein means any one member of a particular list and also comprises any combination of members of that list. The phrase "at least one of A and B" as used herein means "only A, only B, or both A and B"; while the phrase "one of A and B" means "A or B."

To simplify the description of various elements disclosed herein, the conventions of "left," "right," "front," "rear," "top," "bottom," "upper," "lower," "inside," "outside," "inboard," "outboard," "horizontal," and/or "vertical" may be referenced. Unless stated otherwise, "front" describes that end of the transfer system nearest to and occupied by a user of the transfer device; "rear" is that end of the transfer device that is opposite or distal the front; "left" is that which is to the left of or facing left from a person facing towards the front of the transfer device; and "right" is that which is to the right of or facing right from that same person while facing towards the front of the transfer device. "Horizontal" or "horizontal orientation" describes that which is in a plane extending from left to right and aligned with the horizon. "Vertical" or "vertical orientation" describes that which is in a plane that is angled at 90 degrees to the horizontal.

A transfer device and associated methods, systems, devices, and various apparatuses are disclosed herein. The transfer device can comprise a security mechanism. The transfer device can further comprise a docking indicator configured to indicate to a user a state, condition, or position of the security mechanism or a portion thereof.

As shown in FIG. 1, a transfer system 50 can include support platforms 30a,b and a transfer device 100. Either of the support platforms 30a,b can be a stationary support platform or a mobile support platform or can be convertible between stationary and mobile configurations. As shown, the support platform 30a can be the stationary support platform and the support platform 30b can be the mobile support platform. The transfer device 100 can support a patient care apparatus 60 and can transfer the patient care apparatus 60 from the support platform 30a to the support platform 30b and vice versa. For example and without limitation, a support shaft or support post 296 (shown in FIG. 3) of the transfer system 100 can support the patient care apparatus 60. As used in the instant disclosure, the term "transfer" refers to transferring patient support equipment such as the patient care apparatus 60 between support platforms such as, for example and without limitation, the support platforms 30a,b.

The support platform 30a can comprise, for example and without limitation, a wall, a headwall, a ceiling-mounted or wall-mounted boom, a free-standing or movable column or other structure, including that which can be found in a hospital room or other patient treatment facility. The support platform 30b can comprise, for example and without limitation, a patient bed 40 as shown, a gurney; a wheelchair; an ambulance, helicopter, or other vehicle; or another mobile platform. Each of the support platforms 30a,b can comprise a receiver 110a,b, which can be configured to receive and support the transfer device 100. Each of the receivers 110a,b can also be a docking cone in that a shape of an outer surface 111 (shown in FIG. 3) of each of the receivers 110a,b can be at least in part conical or frustoconical. To indicate lockable engagement, i.e., secure docking of the receiver 110a,b inside the transfer device 100, the transfer device can comprise an indicator 120 (shown, e.g., in FIG. 14A) or a set of indicators 120a,b (shown, e.g., in FIG. 3).

As shown, each of the support platforms 30a,b can comprise an arm 70a,b, which can support the respective receiver 110a,b. In some aspects, the receiver 110a can be secured to the arm 70a, and the arm 70a can be secured to a stationary structure such as a wall 91 through, for example and without limitation, a connector 31a or a pole 36 or both the connector 31a and the pole 36. Similarly, the arm 70b can be secured to a mobile structure such as the patient bed 40 by using a connector 31b. The connector 31b can be mated to an accessory bracket 46 of the patient bed 40 via an adapter 49 or other connection.

When treated in a hospital room, a patient can be connected to the patient care apparatus 60. The patient care apparatus 60 can be attached to the transfer device 100, docking cups 175a,b (shown in FIG. 3) of which can be rotatably docked to the respective receivers 110a,b. By articulating the arms 70a,b, the receivers 110a,b, and the connectors 31a,b, the corresponding support platforms 30a,b can be positioned for optimal patient care. When the patient care apparatus 60 is physically detached from the patient bed 40 while the patient is in a room, caregivers can have greater access or even unobstructed access to the patient all around the patient bed 40. As used in the instant disclosure, the term "docking" and "docking maneuver" refers to inserting one of the receivers 110a,b into one of the docking cups 175a,b of the transfer device 100 while the receivers 110a,b and the docking cups 175a,b are generally in coaxial alignment and in a load-bearing relationship. The arms 70a,b can comprise one or more articulating arm segments, which can extend the reach and flexibility of the transfer system 50.

The patient bed 40 can comprise a mattress 42. A height 48 of the mattress 42 relative to a floor 92 or any other height measurement of the patient bed 40 can be adjustable by a lift mechanism 43, which can be powered by any source of power such as, for example and without limitation, an electric motor or hand crank. The patient bed 40 can comprise a height-adjustable frame 41, which can comprise the accessory bracket 46. The accessory bracket 46 can be positioned proximate to a headboard 45 of the patient bed 40. The accessory bracket 46 can be used to secure a variety of accessories such as, for example and without limitation, push handles, foldable IV poles, guide wheels or orthopedic frames, and the transfer device 100 disclosed herein. Any component of the support platform 30b such as, for example and without limitation, the arm 70b can be attached to the accessory bracket 46 of the patient bed 40 or directly to the patient bed 40 by welds, mechanical fasteners, clamps, or other known fastening methods.

Figure 2:
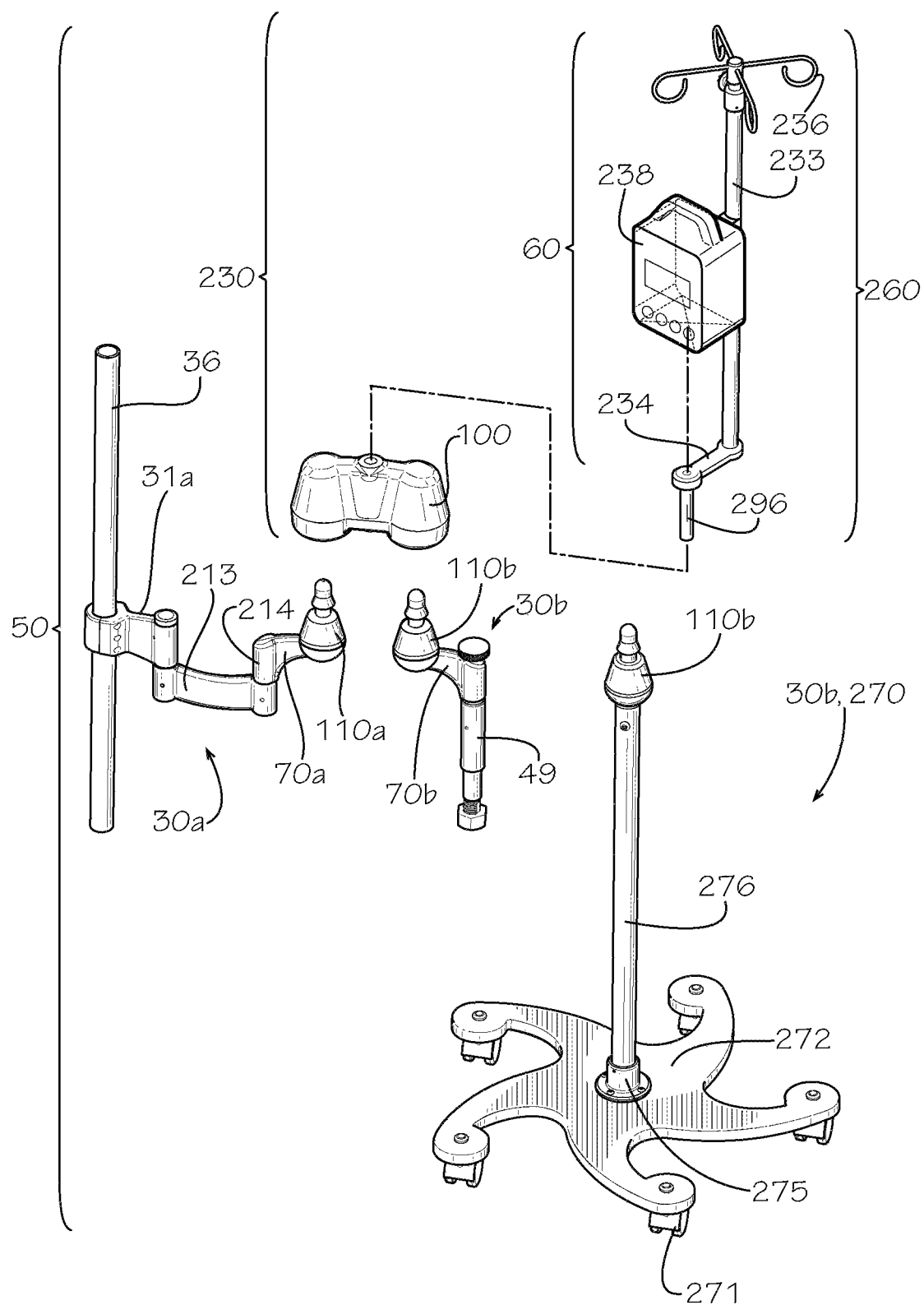
FIG. 2 is a perspective view of a transfer system in accordance with another aspect of the current disclosure.

FIG. 2 discloses the transfer system 50 in accordance with another aspect of the current disclosure. As shown, the transfer system 50 can comprise a transfer apparatus 230, the support platform 30a, and the support platform 30b, which can comprise a mobile stand-alone support platform 270. Various elements of the transfer system 50 can be compatible with the structures disclosed in FIG. 1. With such compatibility, the docking cups 175a,b (shown in FIG. 3) of newer transfer devices 100 including those disclosed herein can receive the receivers 110a,b of older support platforms 30a,30b, and the docking cups 175a,b of older transfer devices 100 can receive the receivers 110a,b of newer support platforms 30a,b.

The transfer apparatus 230 can comprise the transfer device 100 and the patient care apparatus 60. The patient care apparatus 60 can comprise an offset arm 234 and a pole 233, which in some aspects can be an IV pole. The patient care apparatus 60 can comprise a patient care device 238 such as, for example and without limitation, an IV pump as shown. In some aspects, a center of gravity of the patient care device 238 can be located directly over the support post 296. In some aspects, the patient care apparatus 60 can comprise multiple IV poles, hooks 236, one or more IV infusion pumps, or another type of patient care device mountable either directly or indirectly on the pole 233 or the offset arm 234 or another portion of the patient care apparatus 60. In some aspects, a patient care apparatus kit 260 can comprise the patient care apparatus 60 and the support post 296 and can be installed or replaced in the field to change the configuration of the particular patient care apparatus 60 as desired by the user.

The support platform 30a can comprise the pole 36, the connector 31a, a connecting link arm 213, and a receiver arm 214. The arm 70a can comprise the connecting link arm 213 and the receiver arm 214. The brackets used to secure the pole 36 to a nearby stationary structure of the support platform 30a can be configured to support a load measuring as much a hundred pounds or more. The patient care apparatus 60 can weigh in excess of 100 pounds.

The mobile stand-alone support platform 270 can comprise a base 272 and a support pole 276, which can be mounted to the base 272 with a connector 275. The base 272 can comprise a leg support 271, which can be a leg or a caster. With the leg supports 271, the mobile stand-alone support platform 270 to be transported to and between those aforementioned environments where a support platform 30a,b is otherwise not available.

Figure 3:
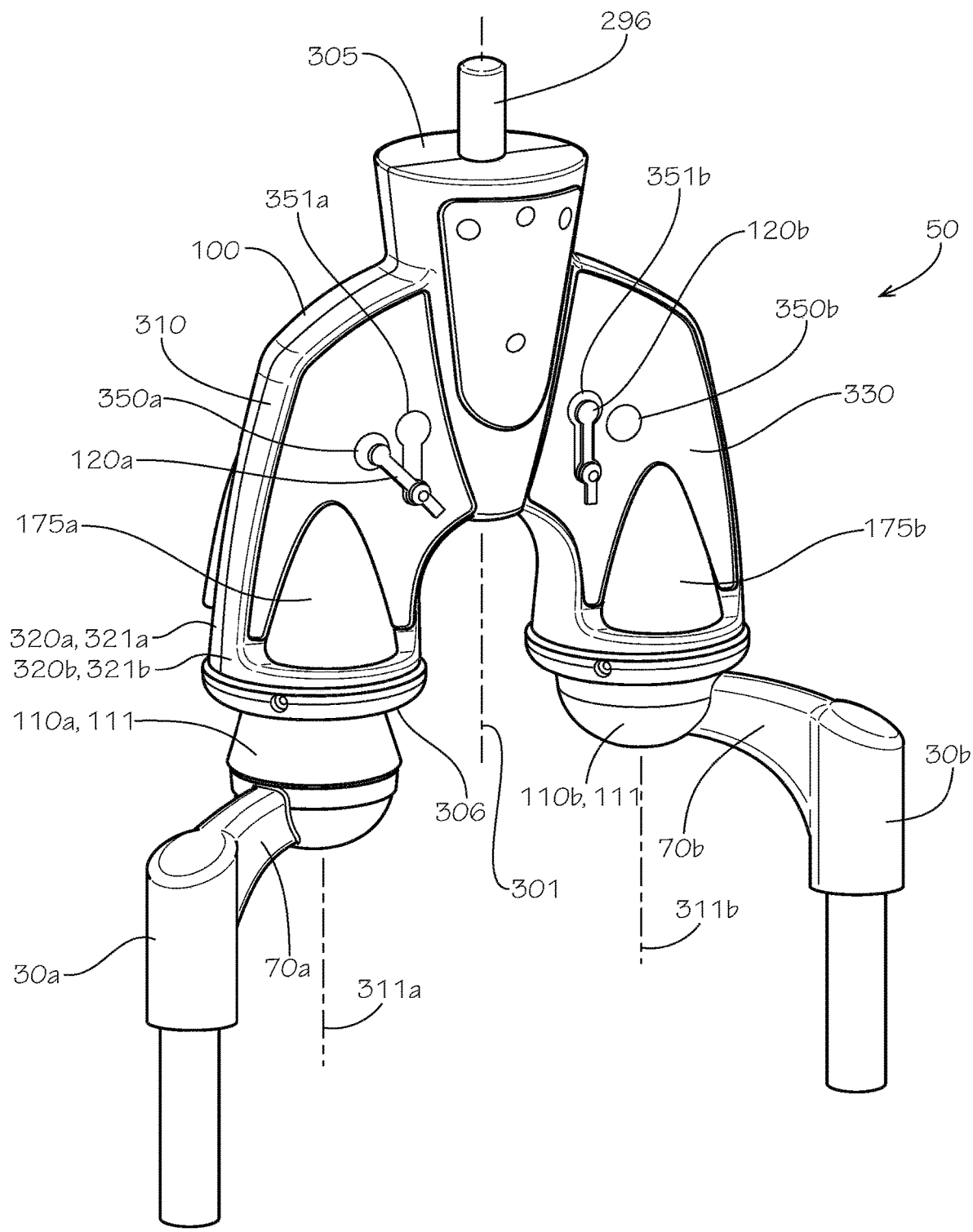
FIG. 3 is a perspective view of the transfer device of FIG. 1 together with a receiver of a first support platform and a receiver of a second support platform.

FIG. 3 is a perspective view of the transfer device 100 together with the receiver 110a of the support platform 30a and the receiver 110b of the support platform 30b. As shown, the transfer device 100 can comprise one or more of the indicators 120a,b, the purpose of which will now be described. The docking cups 175a,b and the receivers 110a,b can be configured to lockably engage with each other. In some conditions, however, misaligned or damaged components of the transfer system 50 can fail to properly dock. More specifically, when sufficiently misaligned or damaged, one component of the transfer system 50 such as the receiver 110a,b can fail to lockably engage with another component of the transfer system 50 such as one of the docking cups 175a,b of the transfer device 100. A position of one or more of the indicators 120a,b can signal to a user of the transfer device 100—and of the transfer system 50 more broadly—that the receiver 110a,b has or has not positively and lockably engaged with the corresponding docking cup 175a,b of the transfer device 100. With this knowledge, the user can correct the misalignment or other issue by adjusting an angle or a height of a portion of the support platform 30b such as the patient bed 40 (shown in FIG. 1) or other structure, take the transfer system 50 offline, and/or alert responsible individuals as appropriate.

As also shown, the receiver 110a is shown disengaged from the docking cup 175a of the transfer device 100, and the receiver 110b is shown engaged with the docking cup 175b of the transfer device 100. Alignment of the indicators 120a,b with marks 350a,b can indicate disengagement and alignment with marks 351a,b can indicate engagement with the docking cups 175a,b. This is reflected in the respective positions of the indicators 120a,b as shown: the indicator 120a corresponding to the receiver 110a is pointing towards a mark 350a indicating disengagement, and the indicator 120b corresponding to the receiver 110b is pointing towards a mark 351b indicating disengagement. The transfer device 100 can comprise a housing 310 defining a top end 305, a bottom end 306, and an axis 301 aligned with the support post 296 and extending from the top end 305 to the bottom end 306. In some aspects, the transfer device 100 and, more specifically, the housing 310 can define a single mark such as the mark 350a,350b or 351a,351b for each of the indicators 120a,b to indicate the aforementioned engagement or disengagement. Alignment with the single mark can indicate engagement (or disengagement, as the case may be, depending on the orientation and design of the mark as a means of communicating meaning to a user) and lack of alignment can indicate disengagement (or engagement, depending on the orientation and design of the mark).

Figure 4:
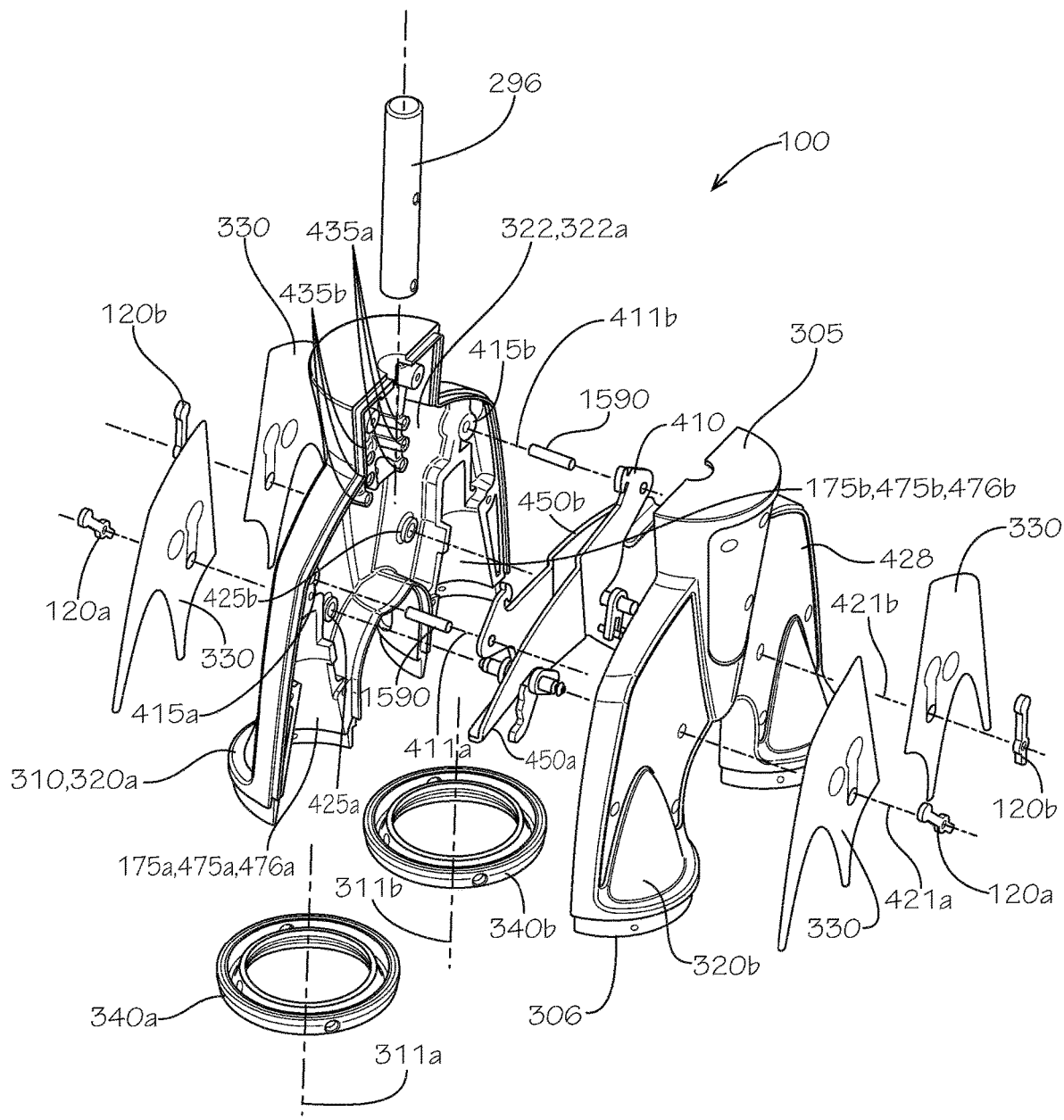
FIG. 4 is a side perspective exploded view of the transfer device of FIG. 3.

In some aspects, as shown, the housing 310 of the transfer device 100 can comprise two housing halves 320a,b, which can be joined along a central joint plane optionally aligned with the axis 301 with assembly fasteners (not shown) to form a generally hollow, thin-walled clamshell housing 310 suitable for cost-effective molding or casting. Each housing half 320a,b can have generally smooth, easy-to-clean exterior surfaces 321a,b and can define label recesses 428 (shown in FIG. 4) to permit covering and sealing the assembly fasteners and other surface irregularities with labels 330 for effective infection control, for a better aesthetic appearance, and as a surface in or on which to provide marks for indicating a position of one or more portions of a security mechanism 410 (shown in FIG. 4). In other aspects, the housing 310 can be formed other than with the housing halves 320a,b and can, for example and without limitation, be formed by an upper housing portion and a lower housing portion joined together as shown in FIGS. 2 and 18A-18D. The interior surfaces 322a,b (322a shown in FIG. 4, 322b shown in FIG. 15B) of housing halves 320a,b or an interior surface 322 of the housing as otherwise formed can define bosses, ribs, and other features. As will be described, such features can cooperate to retain, for example and without limitation, the aforementioned assembly fasteners, pivot pins, and biasing members as well as other structural and/or functional elements such as docking cups 175a,b and the support post 296.

Figure 16A:
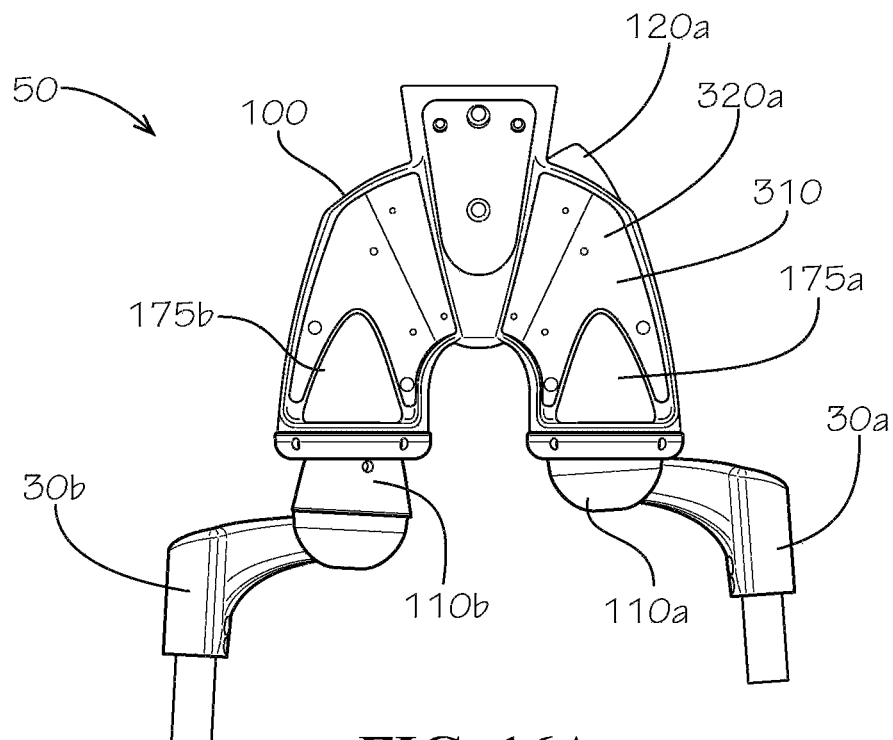
FIG. 16A is a front view of a transfer device together with a receiver of a first support platform and a receiver of a second support platform, the transfer device comprising a set of indicators in accordance with another aspect of the current disclosure and with the set of indicators in a first indicating condition showing the receiver of the first support platform lockably engaged with a first docking cup of the transfer device.
Figure 16B:
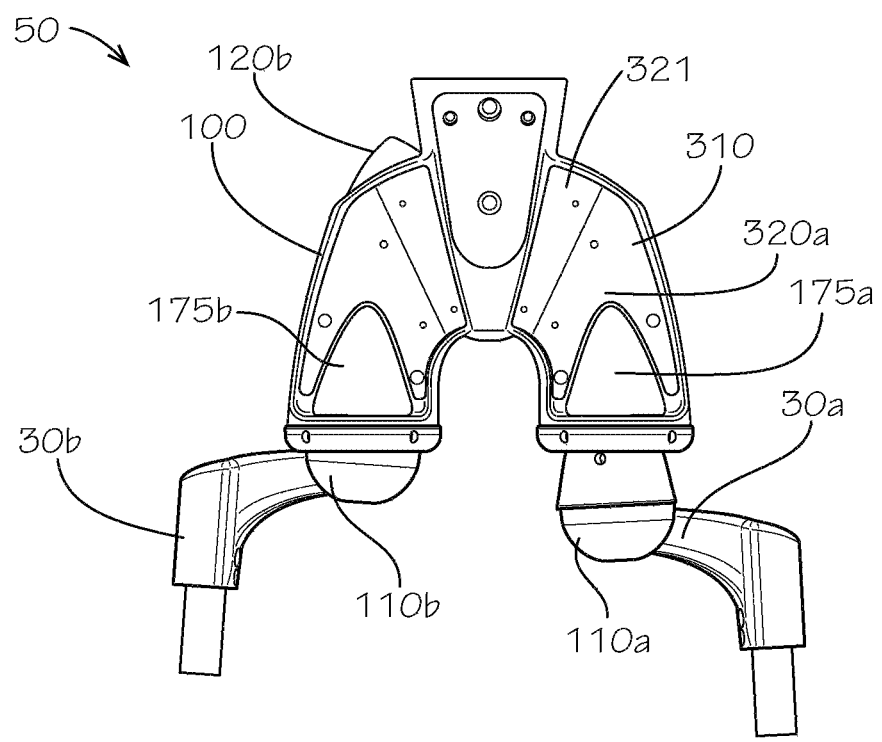
FIG. 16B is a front view of the transfer device and the receivers of FIG. 16A with the set of indicators in a second indicating condition showing the receiver of the second support platform lockably engaged with a second docking cup of the transfer device.

FIG. 4 is a side perspective exploded view of the transfer device 100. As shown, an inner surface 476a,b defined by an inner wall 475a,b of each of the respective docking cups 175a,b can face downward and can be positioned in the two housing halves 320a,b such that docking cups 175a,b are able to receive and are configured to receive the receivers 110a,b as shown in FIG. 3. The docking cups 175a,b can define respective docking cup axes 311a,b, which can be spaced apart sufficiently to avoid interference caused by the support platforms 30a,b (shown in FIG. 3) being in close proximity with each other. The docking cup axes 311a,b may be parallel with respect to each other as shown or, as shown in FIGS. 16A and 16B, converging toward a point. Each of the docking cups 175a,b and, more specifically the inner walls 475a,b and the inner surfaces 476a,b thereof can define a frustoconical cavity, while each of the receivers 110a,b (shown in FIG. 3) can define a frustoconical outer surface. The transfer device 100 and, more specifically, the housing 310 can comprise docking rings 340a,b positioned on the bottom end 306 of the housing 310. As shown, the docking rings 340a,b can define the bottom end 306 of the housing 310. The docking rings 340a,b can be toroid bodies and can terminate, reinforce, and provide accurate concentricity to a bottom opening of each of the docking cups 175a,b.

As shown, the transfer device 100 can comprise first pair and a second pair of the indicators 120a,b. Each of the first pair and the second pair of the indicators 120a,b can be positioned on opposite sides of the transfer device 100 from each other (i.e., the second pair of indicators 120a,b can be positioned on a side of the transfer device 100 that is opposite from a side of the transfer device 100 on which the first pair of the indicators 120a,b is positioned). Moreover, the first pair and the second pair of the indicators 120a,b can be joined to each other via an indicator linkage 610a,b (shown in FIG. 6).

The housing 310 and, in some aspects, more specifically the housing halves 320a,b of the transfer device 100 can enclose the security mechanism 410. The housing halves 320a,b can be aligned with and assembled about the security mechanism 410 and with the indicators 120a,b along assembly axes 421a,b. Each of the housing halves 320a,b can define indicator bosses 425a,b, which can be concentric with the assembly axes 421a,b to help position and retain a portion of the security mechanism 410 coupled to the indicators 120a,b and facilitate smooth and consistent operation of same. The housing halves 320a,b can define security lever bosses 415a,b, which can be concentric with pivot axes 411a,b to help position and retain security levers 450a,b of the security mechanism 410 and facilitate smooth and consistent operation of same. As shown, the security levers 450a,b can be assembled in a reverse relationship with each other and can be retained by and pivot about pivot pins 1590, which can be retained in the bosses 415a,b. The housing halves 320a,b can define attachment points 435a,b, one or more of which can be bosses and can engage with biasing members 570a,b (shown in FIG. 5).

In some aspects, as shown, a pair of biasing members 570a or 570b can extend between the housing and a corresponding security lever 450a,b. In some aspects, a single biasing member 570a,b or more than two biasing members 570a,b can extend between the housing and the corresponding security lever 450a,b. Each of the biasing members 570a,b can be a spring or other biasing structure or element defining a spring constant and configured to store energy. A spring constant of each of the biasing members 570a,b or combination of the biasing members 570a,b can be adjusted to increase or decrease a biasing force resulting from extension of the biasing members 570a,b from their natural positions. In some aspects, as shown, each of the biasing members 570a,b can be a tension spring, which can be configured to be stretched while storing potential energy. In some aspects, each of the biasing members 570a,b can be a compression spring, which can be configured to be compressed while storing potential energy. In some aspects, each of the biasing members 570a,b can be a torsion spring, in which ends of the spring can be configured to rotate while storing potential energy.

Figure 5:
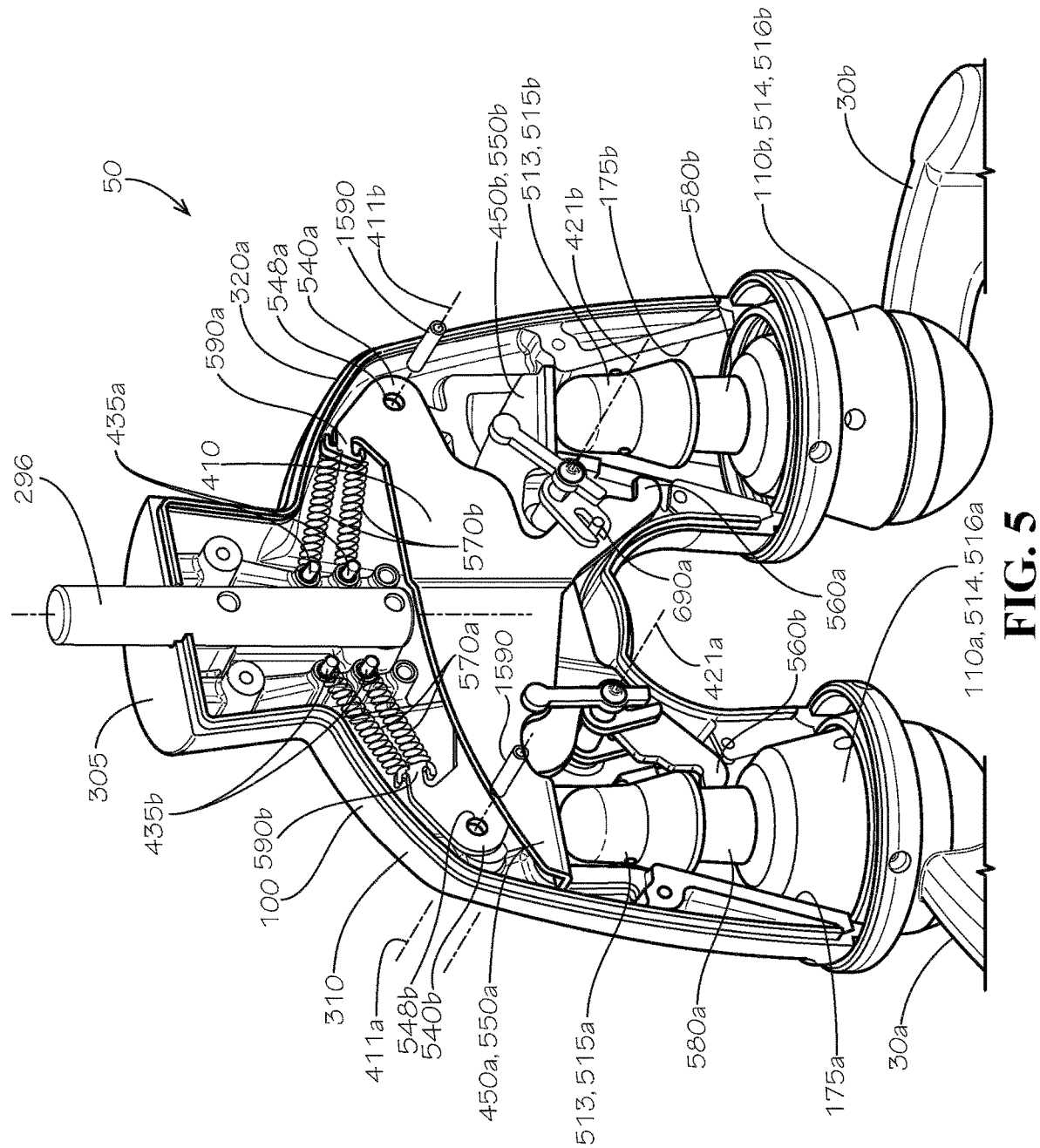
FIG. 5 is a perspective view of the transfer device and receivers of FIG. 3 with a portion of a housing of the transfer device removed.

FIG. 5 is a perspective view of the transfer device 100 and the receivers 110a,b with a portion of the housing 310—and specifically the housing half 320b (shown in FIG. 4)—of the transfer device 100 removed. Each of the receivers 110a,b can define a cylindrical portion 513 at a respective upper end 515a,b, which can define a respective receiver tip or cone tip 517a,b (shown in FIG. 6), and a frustoconical portion 514 at a lower end 516a,b. Between the upper end 515a and the lower end 516b and, in some aspects, between the cylindrical portion 513 and the frustoconical portion 514 the outer surface 111 of each of the receivers 110a,b can step closer to or be offset towards the respective docking cup axis 311a,b to form a security notch 580a,b. The security mechanism 410 and, more specifically, the security levers 450a,b can engage the respective security notches 580a,b in the respective receivers 110a,b.

When engaged, the security mechanism 410 can eliminate the risk of accidentally disconnecting or dislodging the transfer device 100 from the receiver 110*a,b* to which it can be docked. Again, the security mechanism 410 can be fully enclosed inside the housing 310. Each security lever 450*a,b* of the security mechanism 410 can comprise a security latch 560*a,b*, which can pivot as part of the security lever 450*a,b* about a pivot point 548*a,b* defined by a pivot hub or pivot portion 540*a,b* from a first secured position to a second released position, or into and out of engagement with the security notch 580*a,b* of the receivers 110*a,b* to control retention of the receiver 110*a,b* in the respective docking cup 175*a,b* of the transfer device 100. More specifically, the pivot point 548*a,b* can comprise a respective pivot pin 1590. Each security lever 450*a,b* can also comprise a feeler 550*a,b*, which can cause the respective security latch 560*a,b* of the respective security lever 450*a,b* to pivot from the first secured position to the second released position in response to being displaced upward, against the bias of the biasing members 570*a,b*, by the respective upper end 515*a,b* of the receiver 110*a,b*.

When the first receiver 110*a* is in docking engagement with the first docking cup 175*a* of the transfer device 100, the transfer device 100 cannot be removed from the first receiver 110*a* as long as the second docking cup 175*b* is not in docking engagement with the second receiver 110*b*. The transfer device 100 can remain lockably engaged with the first receiver 110*a* in this condition because the absence of the second receiver 110*b* within the second docking cup 175*b* and the feeler 550*b* of the second security lever 450*b* not being lifted or engaged by the second receiver 110*b* can leave the security latch 560*b* of the second security lever 450*b* engaged with the first receiver 110*a* as shown in the first secured position. The security latch 560*b* of the second security lever 450*b* can automatically engage with the security notch 580*a* of the first receiver 110*a* by influence of the aforementioned biasing members 570*a,b*. The biasing members 570*a,b* can by default keep the respective feelers 550*a,b* in a lower position with respect to the respective docking cup 175*a,b* as the security lever 450*a,b* is biased toward the lower position by the respective biasing members 570*a,b*. The biasing members 570*a,b* can pull on respective attachment portions 590*a,b*, each of which can be an attachment hook, towards the respective stationary attachment points 435*a,b* on the housing 310. The biasing members 570*a,b* can thereby tend to rotate or be configured to bias the respective security levers 450*a,b* into locking engagement with the opposite receivers 110*a,b*. As shown, the biasing members 570*a,b* can be engaged with or, more specifically, in contact with the respective security levers 450*a,b*.

Similarly, when the second receiver 110*b* is in docking engagement with the second docking cup 175*b* of the transfer device 100, the transfer device 100 cannot be removed from the second receiver 110*b* as long as first docking cup 175*a* is not in docking engagement with the first receiver 110*a*. Thus, the security mechanism 410 prevents the transfer device 100 from being removed from any one support platform 30*a,b* unless and until the transfer device 100 is docked to another support platform 30*a,b* to which it is being transferred. Only simultaneous, full docking engagement inside both docking cups 175*a,b* by two the receivers 110*a,b* causes the security mechanism 410 to automatically release both of the security latches 560*a,b* from locking engagement with the receivers 110*a,b*, permitting a caregiver the choice of either releasing the transfer device 100 from the receiver 110*a* docked to the docking cup 175*a*, or releasing the transfer device 100 from the receiver 110*b* docked to the docking cup 175*b*. Extracting the receiver 110*a* by even a short distance such as, for example and without limitation, ¼ inch or less from the docking cup 175*a* can cause the security mechanism 410 to engage with the opposite receiver 110*b*, and vice versa.

Figure 6:
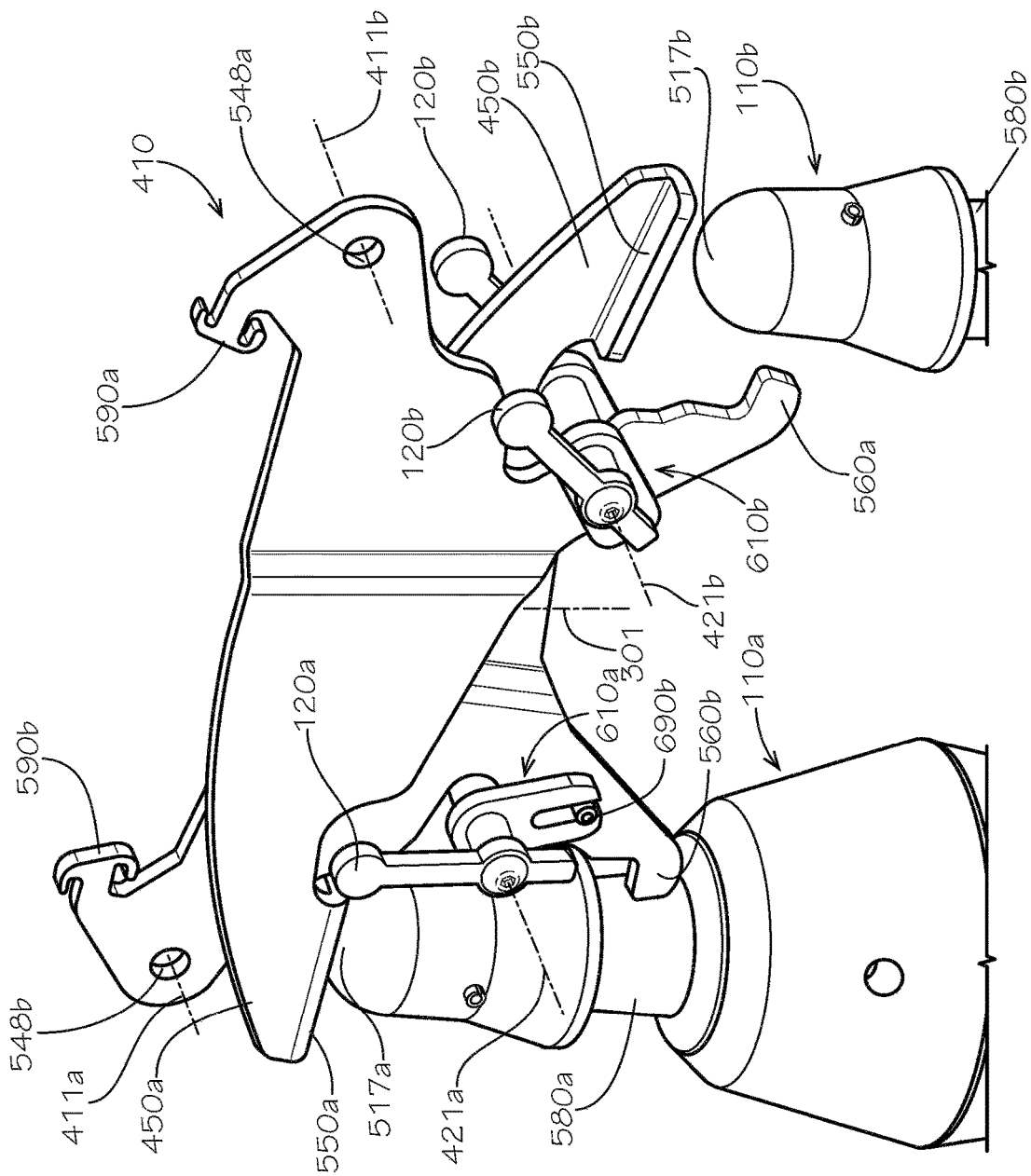
FIG. 6 is a perspective view of the transfer device and the receivers of FIG. 3 with the entire housing of the transfer device and certain other components removed.

FIG. 6 is a perspective view of the transfer device 100 (shown in FIG. 3) and the receivers 110*a,b* with the entire housing 310 (shown in FIG. 3) of the transfer device 100 and certain other components removed. The security levers 450*a,b* can interact with and cause rotation or other movement of the indicators 120*a,b*, depending on the configuration of the indicators 120*a,b*. In some aspects, as shown, this interaction can be via the indicator linkage 610*a,b*.

More specifically, a position or movement of the indicator linkage 610*a* can be controlled by a position or movement of the security lever 450*b*, and a position or movement of the indicator linkage 610*b* can be controlled by a position or movement of the security lever 450*a*. In some aspects, as shown, a pin 690*b*, which can be a guide pin and can extend through a portion of the security lever 450*b* proximate to the security latch 560*b* such as a pin bore 770 (shown in FIG. 7), can extend through and engage with the indicator linkage 610*a*, and movement of the pin 690*b* (which can be caused by movement of the security lever 450*b*) can cause movement—and, in some aspects, rotation—of the indicator linkage 610*a* and thereby also the indicator 120*a*. Similarly, in some aspects, a pin 690*a* (shown in FIG. 5), which can be a guide pin and can extend through a portion of the security lever 450*a* proximate to the security latch 560*a* such as the pin bore 770, can extend through and engage with the indicator linkage 610*b*, and movement of the pin 690*a* (which can be caused by movement of the security lever 450*a*) can cause movement—and, in some aspects, rotation—of the indicator linkage 610*b* and thereby also the indicator 120*b*. In some aspects, as shown, the pins 690*a,b* can be roll, split, or spring pins. In other aspects, the pins 690*a,b* can be another pin or fastener secured to the security lever 450*a,b* or can be formed monolithically with the security lever 450*a,b*. In some aspects, as shown, each of the indicators 120*a,b* can comprise multiple indicators for indicating to the user from multiple sides of the transfer device 100 that the transfer device 100 is or is not lockably engaged with a particular receiver 110*a,b*.

Figure 9:
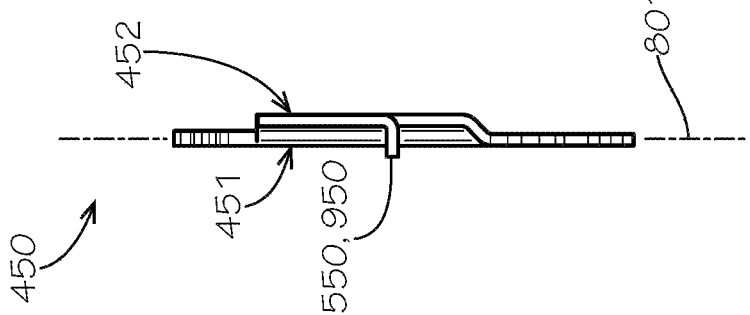
FIG. 9 is an end view of the security lever of FIG. 7 facing an end of the security lever defining a feeler.
Figure 7:
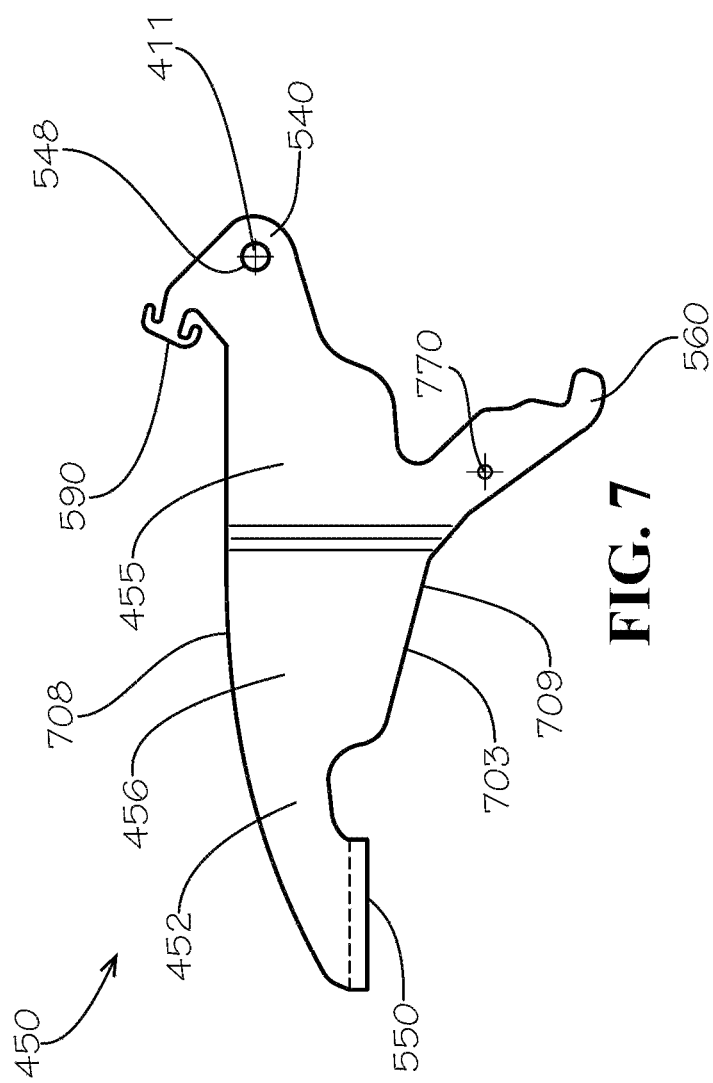
FIG. 7 is a front view of a security lever of a security mechanism of the transfer device of FIG. 3.
Figure 8:
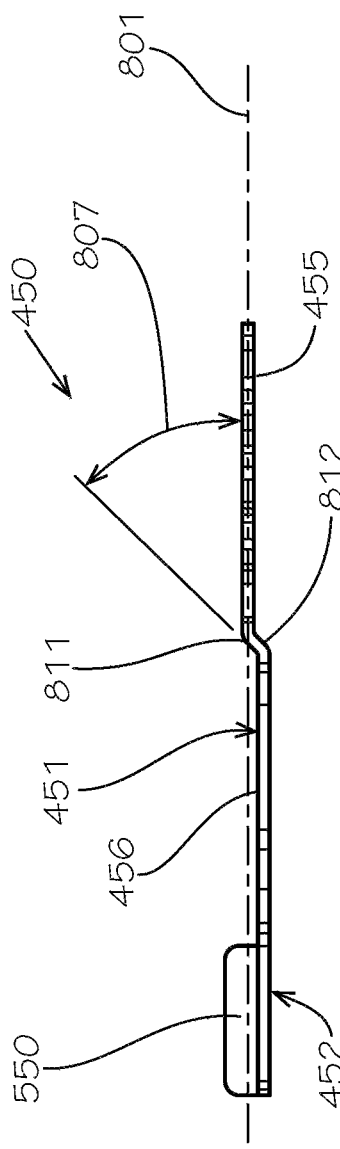
FIG. 8 is a top view of the security lever of FIG. 7.

FIGS. 7-9 show a security lever 450, which can correspond to the security levers 450*a,b* (shown in FIG. 6) of the security mechanism 410 (shown in FIG. 6) of the transfer device 100. More specifically, the security lever 450 shown can correspond to each of the security levers 450*a,b*, which can define the same geometry and be interchangeable with each other. FIG. 7 is a front view of the security lever 450. FIG. 8 is a top view and FIG. 9 is a side view of the security lever 450. As shown in FIG. 7, the security lever 450 can comprise a feeler 550 corresponding to the feelers 550*a,b* and the security latch 560 corresponding to the security latches 560*a,b* of the respective security levers 450*a,b*. The security lever 450 can define a pivot axis 411 and the pivot portion 540, about which the security lever 450 can rotate, corresponding to the pivot portions 540*a,b* of the security levers 450*a,b*. The security lever 450 can further define the attachment portion 590, corresponding to the attachment portions 590*a,b* of the respective security levers 450*a,b*.

The security lever 450 can be a rigid bar or plate defining an inner surface or first side surface 451 (shown in FIG. 8) and an outer surface or second side surface 452 as well as the following corners or "ends" of the security lever 450: the pivot portion 540, the feeler 550, and the security latch 560. As shown in FIG. 8, the security lever 450 can define a set of bends 811 and 812, which can effectively offset a second portion 456 of the security lever 450 with respect to a first portion 455. This offset can minimize the space required for the security mechanism 410, align a centerline 801 (shown in FIG. 8) of the security lever 450 at the pivot portion 540 and the first portion 455 with the corresponding docking cup axis 311a,b, which can be an axis of the corresponding receiver 110a,b, and allow the security levers 450a,b to pass by one other in close proximity without interference. Each of the bends 811 and 812 can define any desirable bend angle including a bend angle 807 of 45 degrees.

The pivot portion 540 can be formed monolithically from the security lever 450 and can define a pivot point 548 corresponding to the pivot points 548a,b of the security levers 450a,b. In some aspects, the pivot point 548a,b can be a bore extending partially or completely through the pivot portion 540 of the security lever 450. In other aspects, the pivot point 548a,b can extend from a surface of the security lever 450 into the housing 310 (FIG. 4) or be otherwise restrained by the housing 310.

In some aspects, the feeler 550 can be formed monolithically from the security lever 450 and can define or be defined by, for example and without limitation, a flange 950 (shown in FIG. 9), which can be bent from the second portion 456 of the security lever 450 as shown. In other aspects, the feeler 550 can be formed from a separate part joined to the security lever 450.

In some aspects, the security latch 560 can be formed monolithically from the security lever 450 and can define a tab, finger, or finger-shaped protrusion sized to be received by and into the corresponding security notch 580a,b (shown in FIG. 5) of the receivers 110a,b.

In some aspects, the security lever 450 can define a simple closed polygonal shape such as that of a rectangle or triangle, particularly if in such case the security lever 450 will not interfere with the housing 310 of the transfer device. In other aspects, as shown in FIG. 7, the security lever 450 can define a relatively complex shape with multiple cutouts along a perimeter 703 of the security lever 450 defining various straight or radiussed edges, which can permit the security lever 450 to reach around or avoid features of the housing 310 such as, for example and without limitation, the inner walls 475a,b (shown in FIG. 4) of the docking cups 175a,b (shown in FIG. 4), the feeler 550 of an adjacent security lever 450, the indicator linkage 610a,b (shown in FIG. 6), and the interior surface 322 (shown in FIG. 4) of the housing 310, which can be in close proximity to the security lever 450. At the same time, a strength of the security lever 450 can be maintained by maximizing the width of various sections (and reducing the aforementioned cutouts), by maximizing a thickness of the security lever 450 itself, or, as will be described, by adjusting the material itself. In some aspects, a thickness of the security lever 450 can be at least 10 gage. In other aspects, the thickness of the security lever 450 can be other than 10 gage. The thickness of the security lever 450 can be substantially constant (i.e., constant other than in locations where deformation during its fabrication may cause variations in thickness).

Pivot pins 1590 (shown in FIG. 4) can be inserted into and extend between security lever bosses 415a,b (shown in FIG. 4) on the interior surfaces 322a,b (322a shown in FIG. 4, 322b shown in FIG. 15B) of first and second housing halves 320a,b (shown in FIG. 4). Each of the security levers 450a,b (shown in FIG. 4) can be rotatably attached to the pivot pins 1590 at the pivot points 548a,b to permit each security lever 450a,b to pivot as previously described. Each of the security levers 450a,b can define an upper edge 708 and a lower edge 709, each of which can extend from the pivot portion 540 to the feeler 550.

Figure 10:
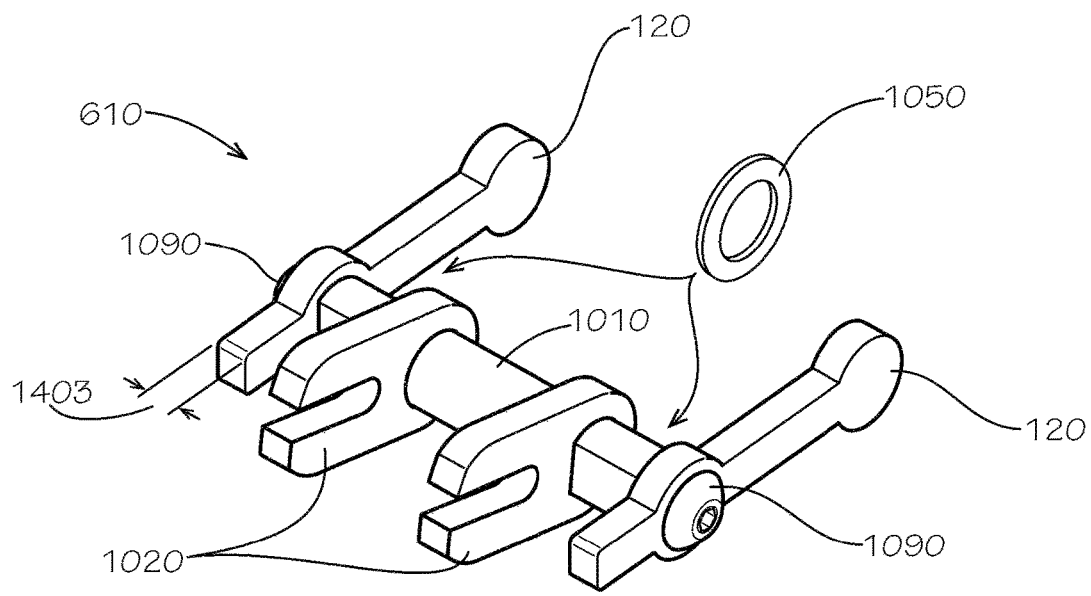
FIG. 10 is a top perspective view of a bottom pivot assembly of the transfer device of FIG. 3A.

FIG. 10 shows the indicators 120 and an indicator linkage 610 to which the indicators 120 can be coupled. The indicator linkage 610 can define and correspond to each of the indicator linkages 610a,b (shown in FIG. 6) of the transfer device 100 (shown in FIG. 5) and can be considered a portion of the security mechanism 410 (shown in FIG. 6). FIG. 10 is a top perspective view of a bottom pivot assembly of the indicator linkage 610 of the transfer device 100. As shown, the indicator linkage 610 can comprise a pivot shaft 1010, a pair of pivot links 1020, a pair of washers or spacers 1050, a pair of the indicators 120, and a pair of indicator fasteners 1090.

As shown, a rotational position of each of the pivot links 1020 and the pair of the indicators 120 can be fixed with respect to the pivot shaft 1010. Moreover, the pair of indicators 120 can be fixably joined to each other via the pivot shaft 1010 of the indicator linkage 610a,b and can be configured to move in unison. In some aspects, the pivot links 1020 can be so fixed with respect to the pivot shaft 1010 with a weld such as, for example and without limitation, a tack weld. In other aspects, the pivot links 1020 can be fixed with respect to the pivot shaft 1010 using a press fit connection between the mating parts. In other aspects, the pivot links 1020 can be so fixed with respect to the pivot shaft 1010 using another fastening method. In some aspects, the indicators 120 can be fixed with respect to the pivot shaft 1010 with the indicator fasteners 1090, each of which can be threaded into a hole defined in the pivot shaft 1010. In other aspects, the indicators 120 can be fixed with respect to the pivot shaft 1010 using a press fit connection between the mating parts or using another fastening method. The indicator linkage 610 can, in any case, rotate in unison about each of the assembly axes 421a,b upon movement of the pins 690a,b (690a shown in FIG. 6, 690b shown in FIG. 5). Each of the spacers 1050 can optionally be positioned between the indicator 120 and the housing 310 (shown in FIG. 4).

Figure 11:
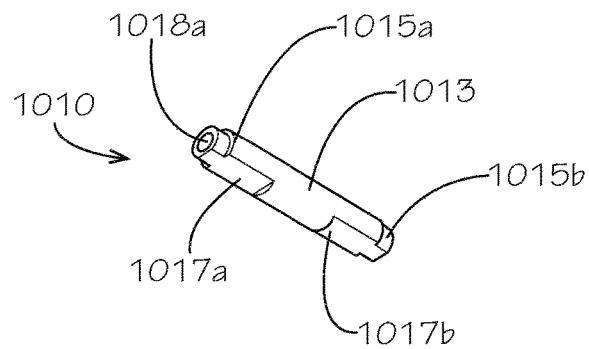
FIG. 11 is a bottom perspective view of a bottom pivot shaft of the bottom pivot assembly of FIG. 10.
Figure 12:
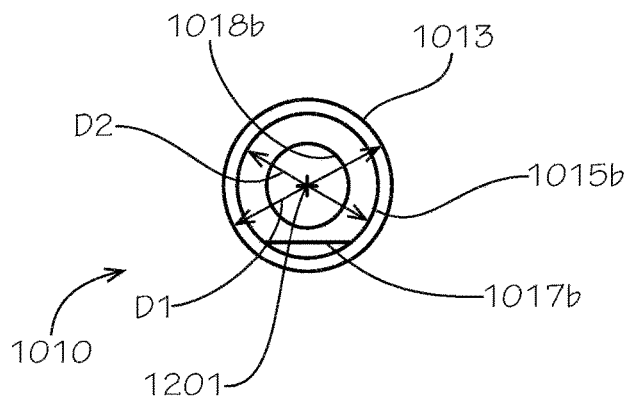
FIG. 12 is an end or front view of the bottom pivot shaft of FIG. 11.

FIGS. 11 and 12 show the pivot shaft 1010, which can be a bottom pivot shaft, of the indicator linkage 610 (shown in FIG. 10). More specifically, FIG. 11 is a bottom perspective view and FIG. 12 is an end or front view of the pivot shaft 1010. As shown, the pivot shaft 1010 can comprise a main portion 1013 defining an outside diameter D1 (shown in FIG. 12) and end portions 1015a,b defining an outside diameter D2 (shown in FIG. 12) positioned on opposite ends of the pivot shaft 1010. In some aspects, a flat 1017a,b—or, more broadly, an anti-rotation element encompassing the flat 1017a,b—can be defined in opposite ends of the main portion 1013 and in each of the respective end portions 1015a,b. In other aspects, the pivot shaft 1010 can be cylindrical in shape throughout its length and can define an axis 1201 (shown in FIG. 12). The pivot shaft 1010 can further define a bore 1018a,b (1018b shown in FIG. 12) in opposite ends. Each of the bores 1018a,b can be sized to receive one of the indicator fasteners 1090a,b and can be threaded. The flats 1017a,b can prevent the pivot links 1020 (shown in FIG. 13) and the indicators 120 (shown in FIGS. 14A-140) from rotating with respect to the pivot shaft 1010 and can thereby keep the pivot links 1020 and the indicators 120 aligned with each other for reliable and consistent indication of engagement or non-engagement of the security mechanism 410 (shown in FIG. 6).

Figure 13:
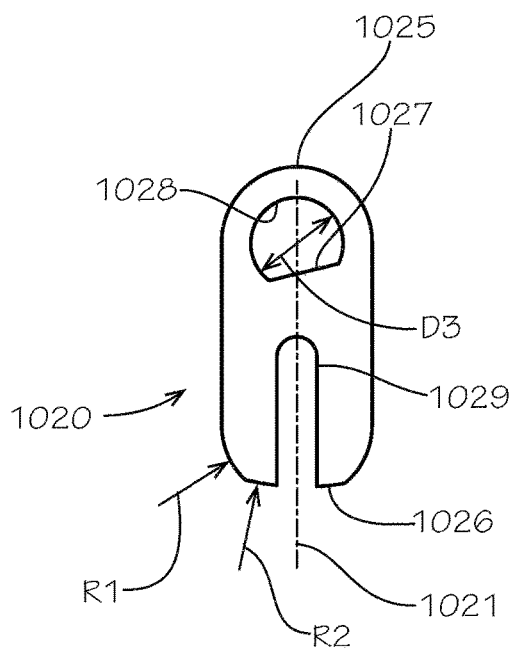
FIG. 13 is a face or side view of a bottom pivot link of the bottom pivot assembly of FIG. 10.

FIG. 13 shows a face or side view of the pivot link 1020 of the indicator linkage 610 (shown in FIG. 10). Each of the pivot links 1020, which can be a bottom pivot link, can define a first end 1025 and a second end 1026. The pivot link 1020 can define an attachment bore 1028 proximate to the first end 1025 and a slot 1029 proximate to the second end 1026. The attachment bore 1028, which can define an inside diameter D3 and a flat 1027, which can be angled with respect to a longitudinal centerline or axis 1021 of the pivot link 1020. In some aspects, the pivot link 1020 can be symmetric about the axis 1021. In other aspects, the pivot link 1020 can be non-symmetric about the axis 1021. The attachment bore 1028 can be sized to fit—with a press fit or more loosely as desired—the middle portion 1013 (shown in FIG. 11) of the pivot shaft 1010 (shown in FIG. 11) and the flat 1027 can be positioned to achieve the desired orientation of the indicator 120 (shown in FIG. 10) with respect to the housing 310 (shown in FIG. 4) and the corresponding label 330 (shown in FIG. 3) upon assembly of the transfer device 100 (shown in FIG. 3). More specifically, the inside diameter D3 of the attachment bore 1028 can in some aspects be equal to the outside diameter D1 of the pivot shaft 1010. The slot 1029 can be sized to slideably fit the pins 690*a,b* (690*a* shown in FIG. 6, 690*b* shown in FIG. 5) to facilitate rotation of the indicator linkage 610 during disengagement and engagement of the receivers 110*a,b* (shown in FIG. 1) with the transfer device 100. The second end 1026 can further define radii R1 and R2 or be otherwise shaped to avoid interference with surrounding parts during use. Symmetry of the pivot link 1020 and placement of the flat 1027 can result in each of the pivot links 1020 of the transfer device 100 being the same and therefore interchangeable.

Figure 14A:
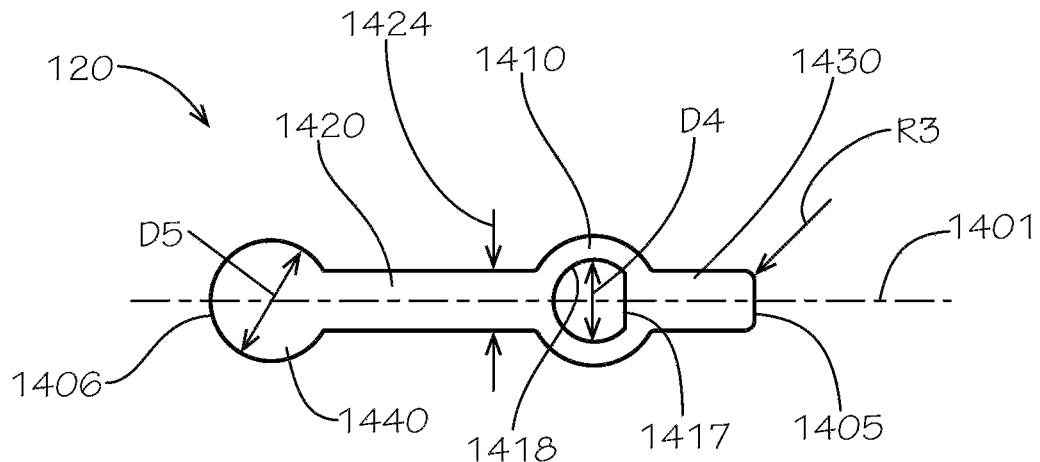
FIG. 14A is a front view of an indicator of the bottom pivot assembly of FIG. 10.
Figure 14B:
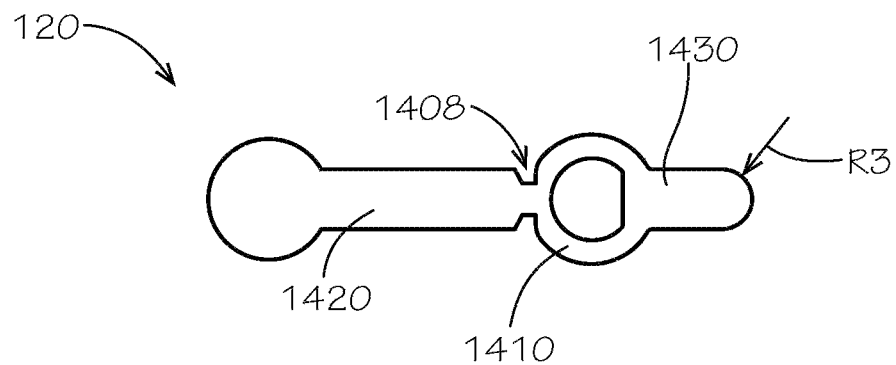
FIG. 14B is a front view of the indicator of the bottom pivot assembly of FIG. 10 in accordance with another aspect of the current disclosure.

FIGS. 14A and 14B show the indicator 120 of the transfer device 100 (shown in FIG. 3). FIG. 14A is a front view of the indicator 120 as shown in earlier figures. The indicator 120, which in some aspects can be a pointer as shown, can comprise a mounting hub 1410 and a first portion 1420 and a second portion 1430, each of which can extend in opposite directions from the mounting hub 1410. Either of the first portion 1420 and the second portion 1430 can extend radially outward from the mounting hub 1410. The indicator 120 can define a first end 1405 and a second end 1406. The indicator 120 can define an attachment bore 1418, which can define an inside diameter D4 and a flat 1417, which can be angled with respect to a longitudinal centerline or axis 1401 of the indicator 120. In some aspects, the indicator 120 can be symmetric about the axis 1401. In other aspects, the indicator 120 can be non-symmetric about the axis 1401. The attachment bore 1418 can be sized to fit—with a press fit or more loosely as desired—the corresponding end portions 1015*a,b* (shown in FIG. 11) of the pivot shaft 1010 (shown in FIG. 11) and the flat 1417 can be positioned to achieve the desired orientation of the indicator 120 with respect to the housing 310 (shown in FIG. 3) and the corresponding label 330 (shown in FIG. 3) upon assembly of the transfer device 100. Any of the indicator 120 or the indicators 120*a,b* (shown in FIG. 3) can point in a direction angled with respect to the horizontal. In some aspects, any of the indicator 120 or the indicators 120*a,b* (shown in FIG. 3) can point upwards, i.e., above the horizontal. In some aspects, any of the indicator 120 or the indicators 120*a,b* can point downwards, i.e., below the horizontal.

More specifically, the inside diameter D4 of the attachment bore 1418 can in some aspects be equal to the outside diameter D2 (shown in FIG. 11) of the pivot shaft 1010. Either of the first portion 1420 and the second portion 1430 can comprise a shaped end 1440 at an end distal from the mounting hub 1410. In some aspects, as shown, the shaped end 1440 of the first portion 1420 can define a round or bulbous shape defining a diameter D5, which can be greater than a width 1424 of the first portion 1420; and a width of the second portion 1430 can be continuous throughout except for radiussed corners defining a radius R3 at the first end 1405. In other aspects, the shaped end 1440 of either of the first portion 1420 and the second portion 1430 can define a non-circular shape, a relative width or diameter of which can be other than that shown. A thickness 1403 (shown in FIG. 10) of the indicator 120 can equal a length or depth of the end portions 1015*a,b* of the pivot shaft 1010 in a longitudinal direction along the axis 1201 (shown in FIG. 12) of the pivot shaft 1010. Symmetry of the indicator 120 and placement of the flat 1417 can result in each of the indicators 120 of the transfer device 100 being the same and therefore interchangeable.

FIG. 14B shows the front view of the indicator 120 of the indicator linkage 610 of FIG. 10 in accordance with another aspect of the current disclosure. As shown, the indicator 120 can define a notch or notches 1408 at an intersection between the mounting hub 1410 and the first portion 1420 or elsewhere on the first portion 1420. The notches 1408, which due to a resulting reduced width of the indicator 120 below the width 1424 (shown in FIG. 14A) can create a weakened area, can allow the indicator 120 to bend if the user manually pushes the indicator 120 with sufficient force. More specifically, each indicator 120 can be configured to fail at the weakened area upon contact with a load that would tend to damage a connection between the indicator 120 and a remaining portion of the transfer device 100. More specifically, each indicator 120 can be configured to deform first at the weakened area upon contact with such a load. The force at which the indicator 120 bends or otherwise deforms can be set at a force less than a force sufficient to damage any of the other components of the transfer device including any other components of the security mechanism 410 (shown in FIG. 6), most of which are housed inside the housing of the 310 of the transfer device 100 (shown in FIG. 3) and more difficult to replace, at least without removing the labels 330 (shown in FIG. 3) and disassembling the transfer device 100. In contrast, if one of the indicators 120 is damaged, it can be easily replaced by simple removal of the indicator fastener 1090 (shown in FIG. 10). As also shown, the radius R3 can be sufficiently large—approaching or equaling a full radius of the second portion 1430—to minimize potential snagging of patient IV lines or other medical equipment.

Figure 14C:
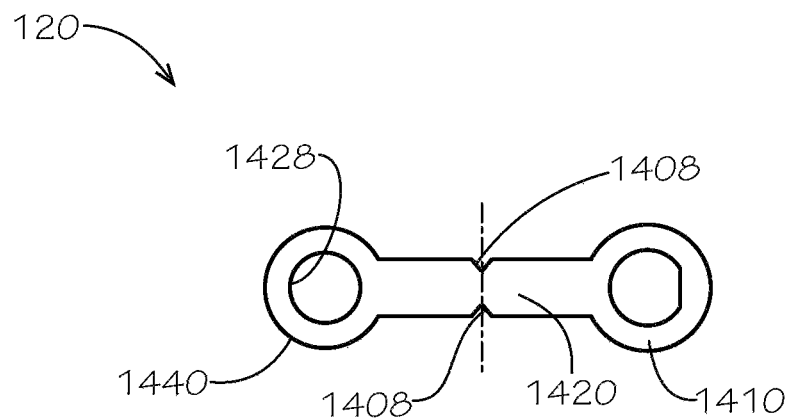
FIG. 14C shows a front view of the indicator of the bottom pivot assembly of FIG. 10 in accordance with another aspect of the current disclosure.

FIG. 14C shows a front view of the indicator 120 of the indicator linkage 610 (shown in FIG. 10) of FIG. 10 in accordance with another aspect of the current disclosure. As shown, a weakened area such as, for example and without limitation, the notches 1408 can be defined in a middle of a length of the first portion 1420 of the indicator 120. As also shown, the shaped end 1440 of the indicator 120 can define a bore 1428, which can reveal a portion of the label 330 (shown in FIG. 3) such as the marks 350*a,b* or 351*a,b* to help indicate whether the security mechanism 410 (shown in FIG. 4) is or is not engaged.

Figure 15A:
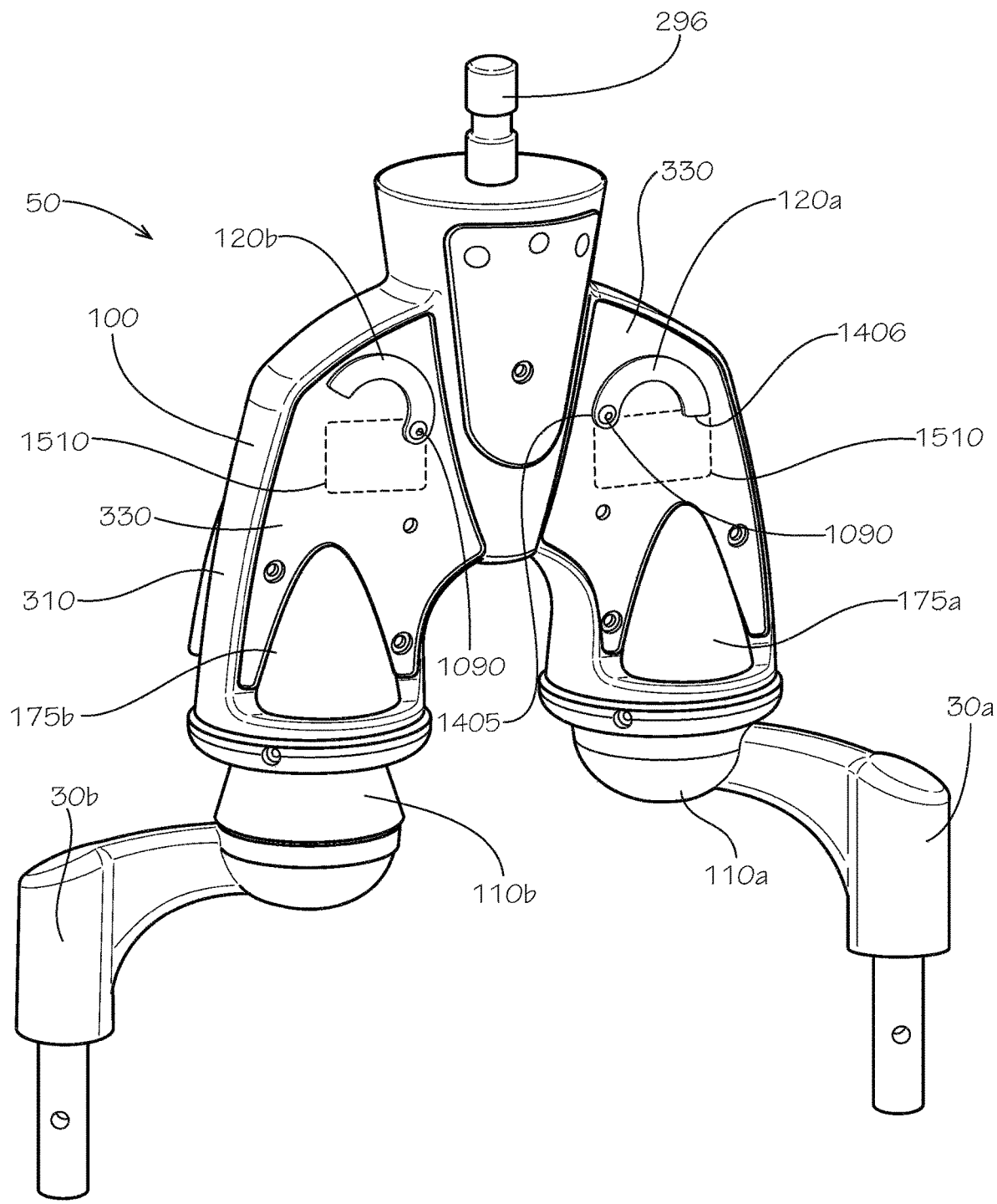
FIG. 15A is a front perspective view of a transfer device together with the receiver of a first support platform and the receiver of a second support platform, the transfer device comprising a set of indicators in accordance with another aspect of the current disclosure and with the set of indicators in a first indicating condition showing the receiver of the first support platform lockably engaged with a first docking cup of the transfer device.
Figure 15B:
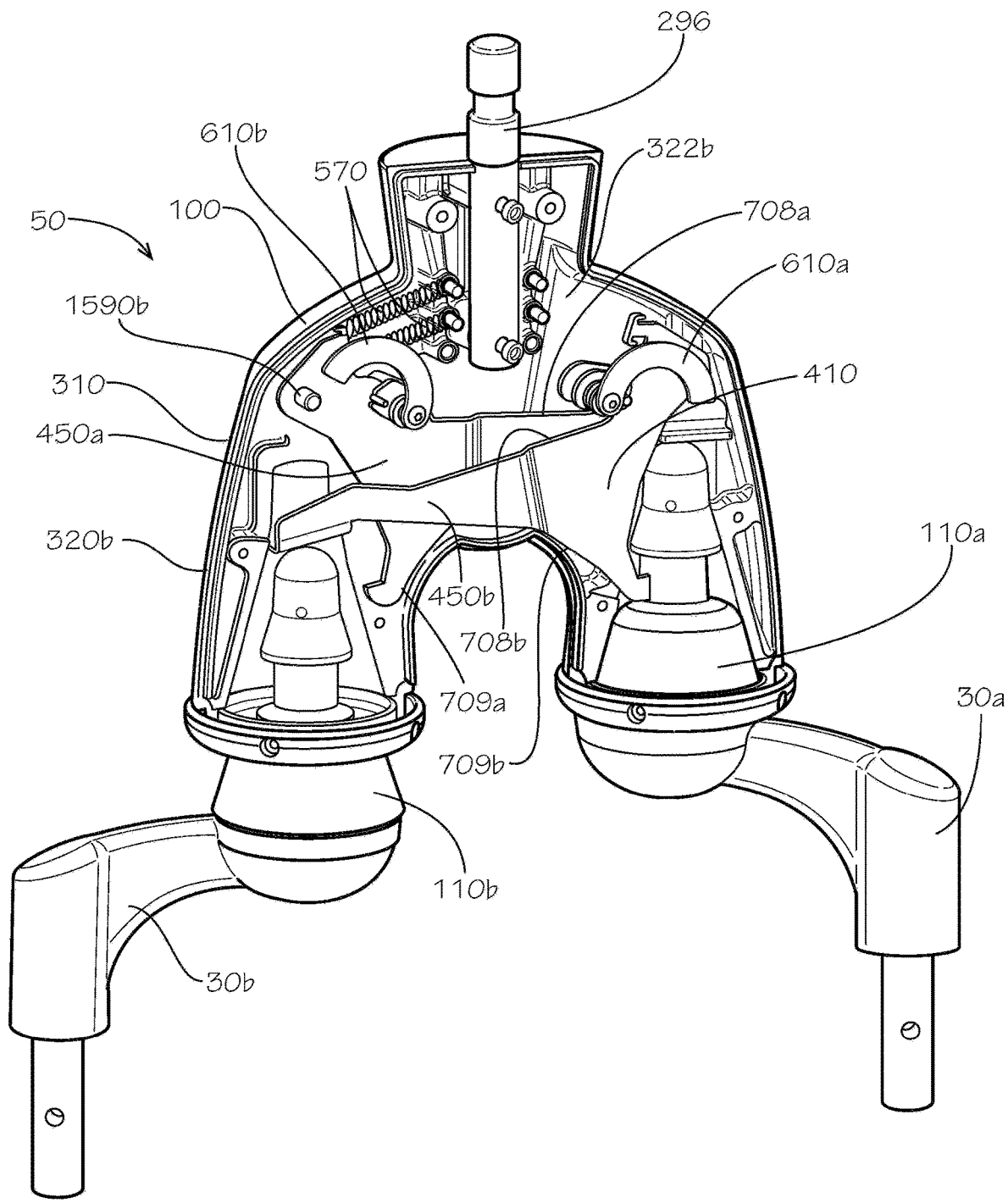
FIG. 15B is a front perspective view of the transfer device and the receivers of FIG. 15A with a portion of the housing of the transfer device removed.
Figure 15C:
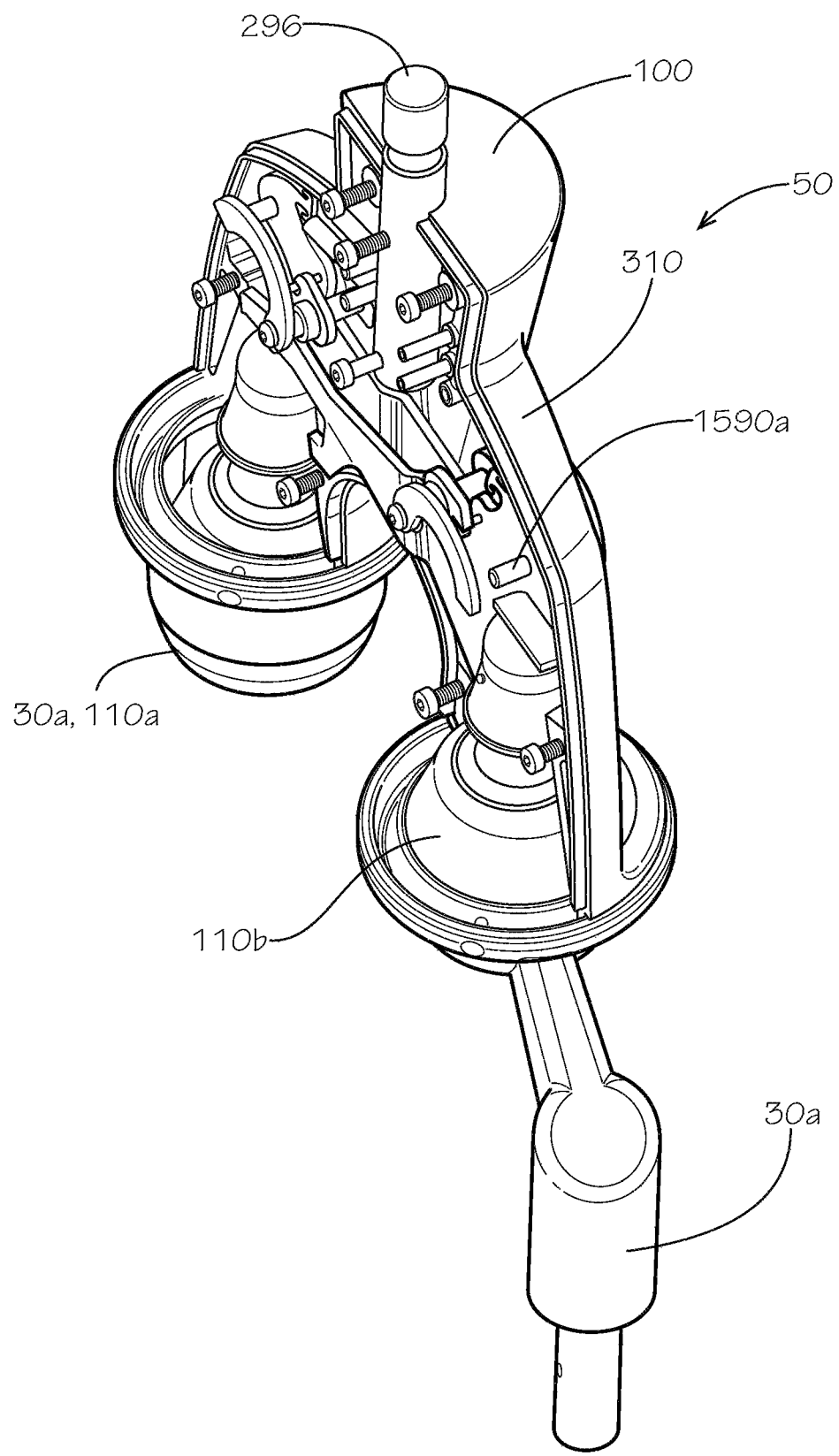
FIG. 15C is a side top perspective view of the transfer device and the receivers of FIG. 15A.

FIGS. 15A-15C show a front perspective view of the transfer device 100 together with the receiver 110*a* of the first support platform 30*a* and the receiver 110*b* of the second support platform 30*b* and comprising a set of the indicators 120*a,b* in accordance with another aspect of the current disclosure. FIG. 15A specifically shows the transfer device 100 with the indicators 120*a,b* in a first indicating condition showing the receiver 110*a* of the first support platform 30*a* lockably engaged with a first docking cup 175*a* of the transfer device. As shown, each of the indicators 120*a,b* can be curved and of a constant width and can be otherwise shaped to resemble a shackle of a padlock, while a surface of the housing 310 of the transfer device 100 or the label 330 can be marked to show a body 1510 of the "padlock," which can be rectangular or any other recognizable padlock shape. As reflected in a position of the "shackle" of the padlock, i.e., an indicator such as the indicator 120a can be shown as engaged or locked when the first end 1405 and the second end 1406 of the indicator 120 are level and otherwise can be shown as disengaged or unlocked such as a position of the indicator 120b as shown.

FIG. 15B shows a front perspective view and FIG. 15C shows a side top perspective view of the transfer device 100 and the receivers 110a,b with a portion of the housing 310 of the transfer device 100 removed. As shown, the position, orientation, and operation of the security levers 450a,b can be as described above, but the indicator linkages 610a,b can be upper pivot assemblies or linkages positioned above the security levers 450a,b instead of below the security levers 450a,b. As shown, the pins 690a,b can extend through a portion of the respective security levers 450a,b that is proximate to the upper edges 708a,b of the respective security levers 450a,b instead of proximate to the lower edges 709a,b of the security levers 450a,b as shown in FIG. 7.

FIG. 16A is a front view of the transfer device 100 together with the receiver 110a of the first support platform 30a and the receiver 110b of the second support platform 30b, the transfer device 100 comprising a set of indicators 120a,b (120b shown in FIG. 16B) in accordance with another aspect of the current disclosure. More specifically, the set of indicators 120a,b are shown in a first indicating condition showing the receiver 110a of the first support platform 30a lockably engaged with the first docking cup 175a of the transfer device 100.

FIG. 16B is a front view of the transfer device 100 and the receivers 110a,b with the set of indicators 120a,b in a second indicating condition showing the receiver 110b of the second support platform 30b lockably engaged with the second docking cup 175b of the transfer device 100. In some aspects, as shown in both FIGS. 16A and 16B, the indicator 120a,b can extend from a top end or top surface of the housing 310 through a seam or opening, which can be defined by an intersection between the housing halves 320a,b (320b shown in FIG. 4). As shown, such a portion of the housing 310 can be upward facing. Each of the indicators 120a,b can be a flag that is raised upon engagement and lowered upon disengagement of the respective receiver 110a,b with the transfer device 100. As with other aspects of the indicators 120a,b disclosed herein, the indicator 120a,b, including when shown as a flag, can be colored to indicate engagement (and safe docking) of the transfer device 100 on the respective receiver 110a,b with a color such as green, which is commonly used to indicate safety or a safe condition. In contrast, the indicator 120a,b, including when shown as a flag, can be colored to indicate disengagement (and incomplete docking) of the transfer device 100 on the respective receiver 110a,b with a color such as red, which is commonly used to indicate caution, danger, or an unsafe condition. In other aspects, pins (not shown) secured to the security levers 450a,b or tips of lengthened security levers 450a,b (shown in FIG. 4) can extend through an opening such as a slot defined in sides of the housing 310 and by their position outside or proximate to the exterior surface 321 of the housing 310 can indicate engagement or disengagement of the security levers 450a,b.

FIGS. 17A-17E show the transfer device 100 together with the receiver 110a of the first support platform 30a and the receiver 110b of the second support platform 30b, the transfer device 100 comprising a set of indicators 120a,b in accordance with another aspect of the current disclosure.

Figure 17A:
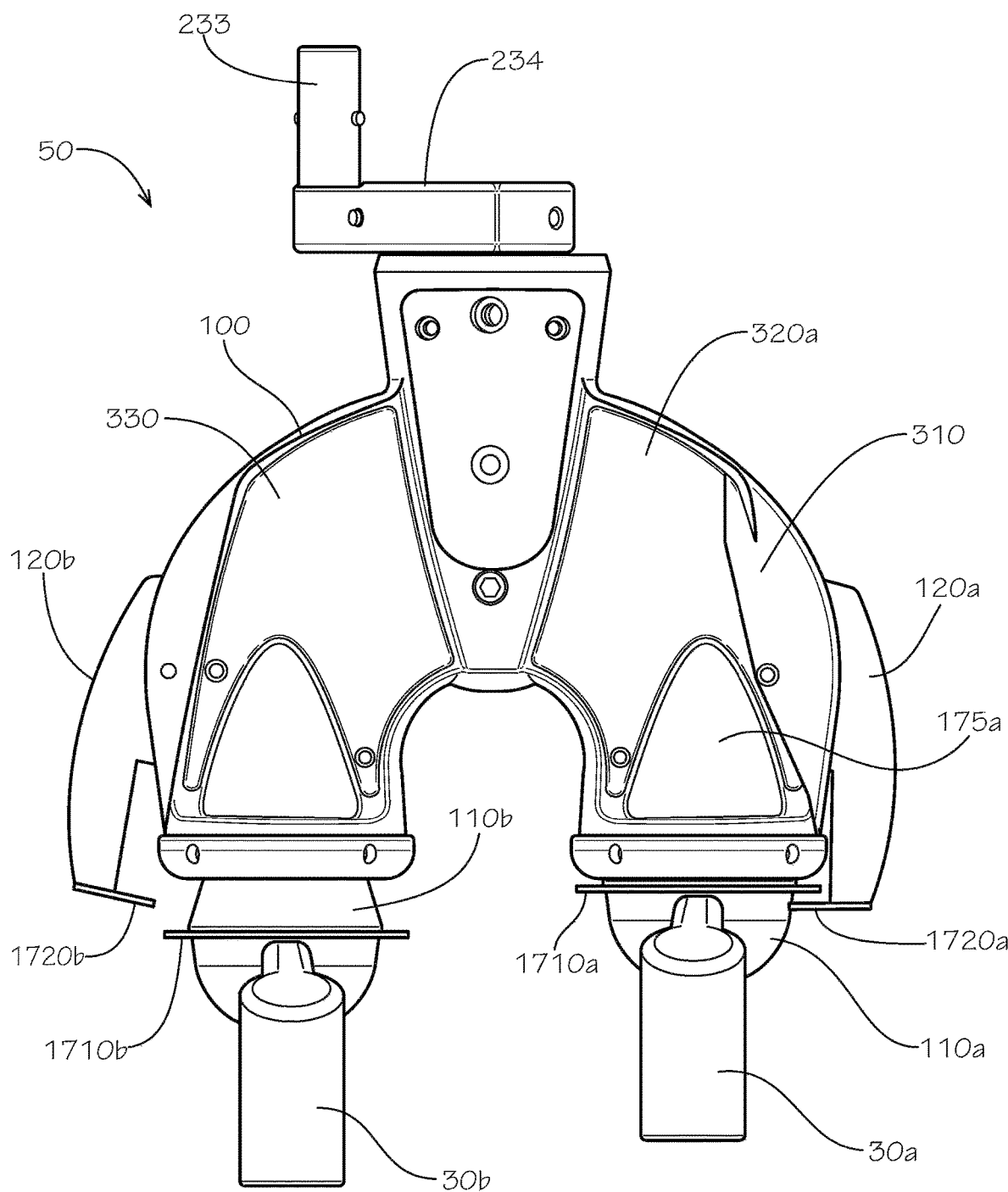
FIG. 17A is a front view of a transfer device together with a receiver of a first support platform and a receiver of a second support platform, the transfer device comprising a set of indicators in accordance with another aspect of the current disclosure and with the set of indicators in a first indicating condition showing the receiver of the first support platform lockably engaged with the first docking cup of the transfer device.

FIG. 17A specifically shows a front view of the transfer device 100 with the set of indicators 120a,b in a first indicating condition showing the receiver 110a of the first support platform 30a lockably engaged with the first docking cup 175a of the transfer device 100. As shown, each of the receivers 110a,b can comprise a shoulder or flange 1710a,b, and each of the indicators 120a,b can comprise a respective catch 1720a,b, which can secure or maintain engagement of the indicator 120a,b and thereby also the transfer device 100 with the respective receiver 110a,b. As shown, each of the indicators 120a,b can extend from a side or side facing surface of the housing 310 through a seam or opening, which can be defined by an intersection between the housing halves 320a,b (320b shown in FIG. 4).

Figure 17B:
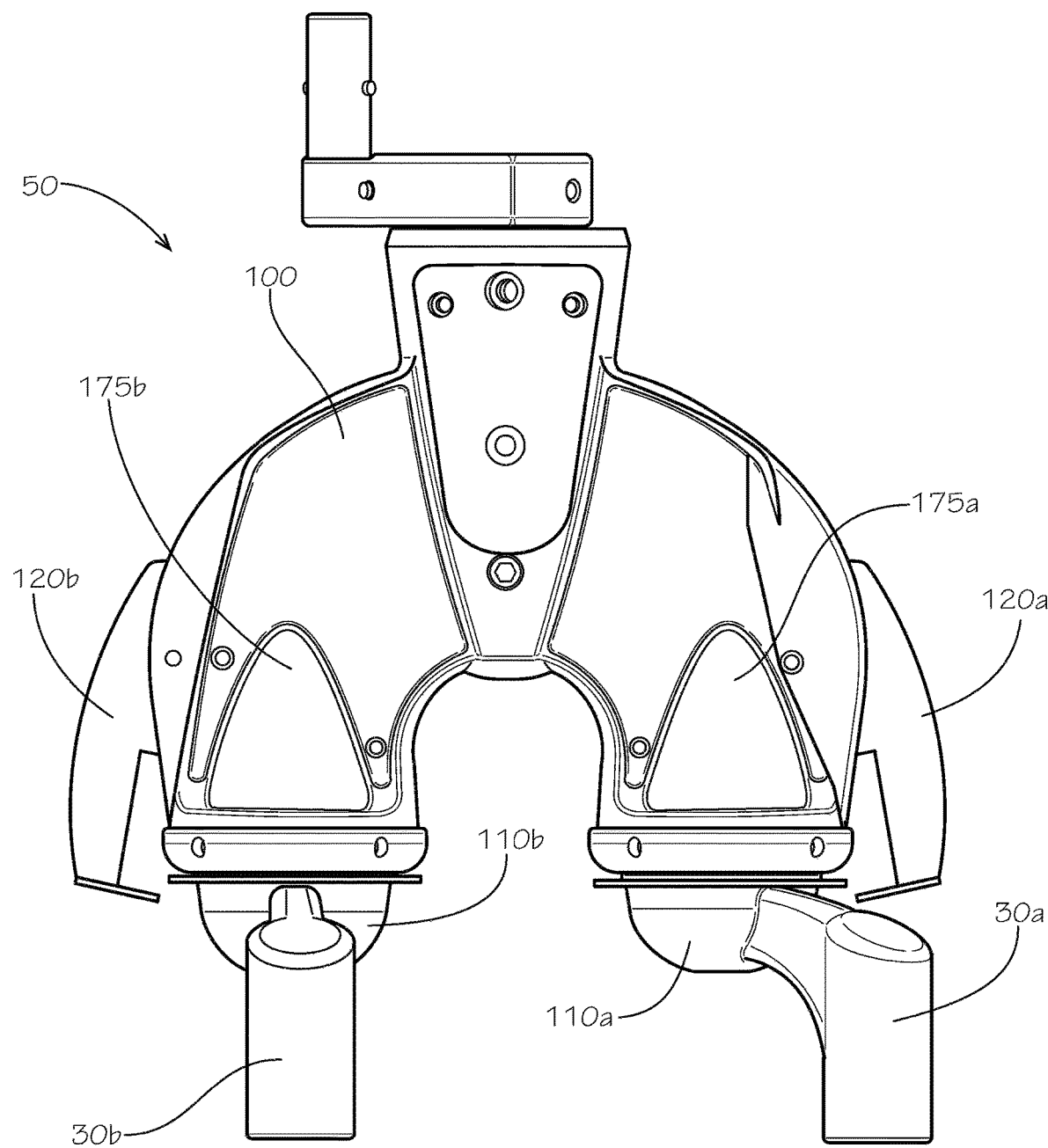
FIG. 17B is a front view of the transfer device and the receivers of FIG. 17A with the set of indicators in a second indicating condition showing both of the receivers engaged but not lockably engaged with respective first and second docking cups of the transfer device.

FIG. 17B shows a front view of the transfer device 100 and the receivers 110a,b with the set of indicators 120a,b in a second indicating condition showing both of the receivers 110a,b engaged but not lockably engaged with respective first and second docking cups 175a,b of the transfer device 100.

Figure 17C:
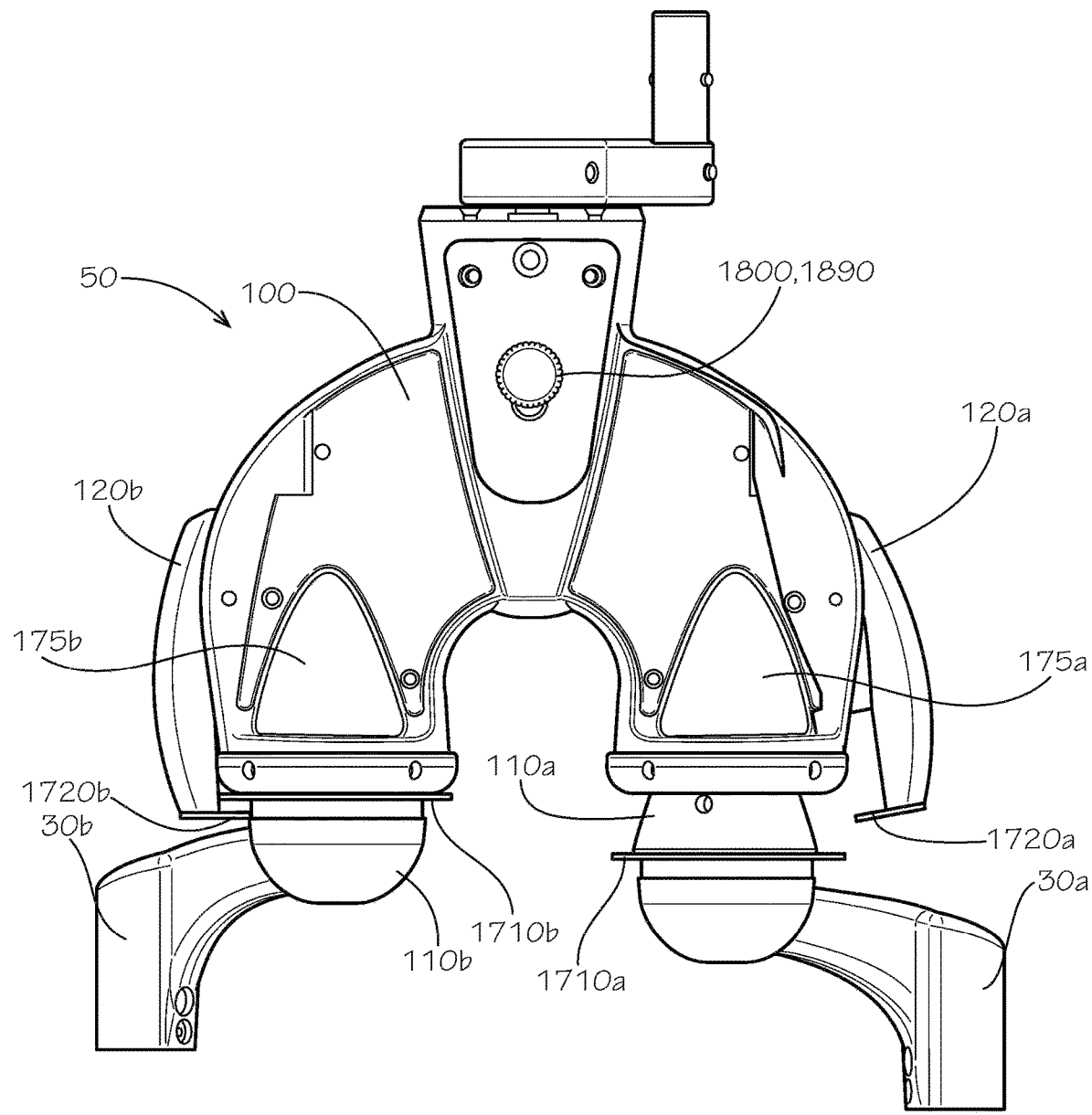
FIG. 17C is a front view of the transfer device and the receivers of FIG. 17A with the set of indicators in a third indicating condition showing the receiver of the second support platform lockably engaged with the second docking cup of the transfer device in accordance with another aspect of the current disclosure.

FIG. 17C shows a front view of the transfer device 100 and the receivers 110a,b with the set of indicators 120a,b in a third indicating condition showing the receiver 110b of the second support platform 30b lockably engaged with the second docking cup 175b of the transfer device 100 in accordance with another aspect of the current disclosure. As shown, the indicators 120a,b can incorporate both two colors to contrast a condition of engagement with a condition of disengagement.

FIG. 17D shows a front perspective view of the transfer device 100 with at least a portion of the housing 310 of the transfer device 100 removed. The attachment portions 590a, b, which can be attachment holes as shown, can receive ends of the biasing members 570a,b (shown in FIG. 5).

FIG. 17E shows a front exploded perspective view of the indicator 120 and the security lever 450 of the security mechanism 410 of the transfer device 100 of FIG. 17A. As shown, the feeler 550 need not comprise the flange 950 (shown in FIG. 9). In addition, instead of the pin 690 being secured to the security lever 450, the pin 690 can be secured to the indicator 120, which here is shown as a rotating flag, and can slideably engage with a pivot slot 1780 defined in the security lever 450. In some aspects, the catch 1720 can be formed separately from and secured to a body 1705 of the indicator 120. In other aspects, the catch 1720 can be formed monolithically as part of a single-piece, i.e., monolithic, indicator 120.

Figure 18A:
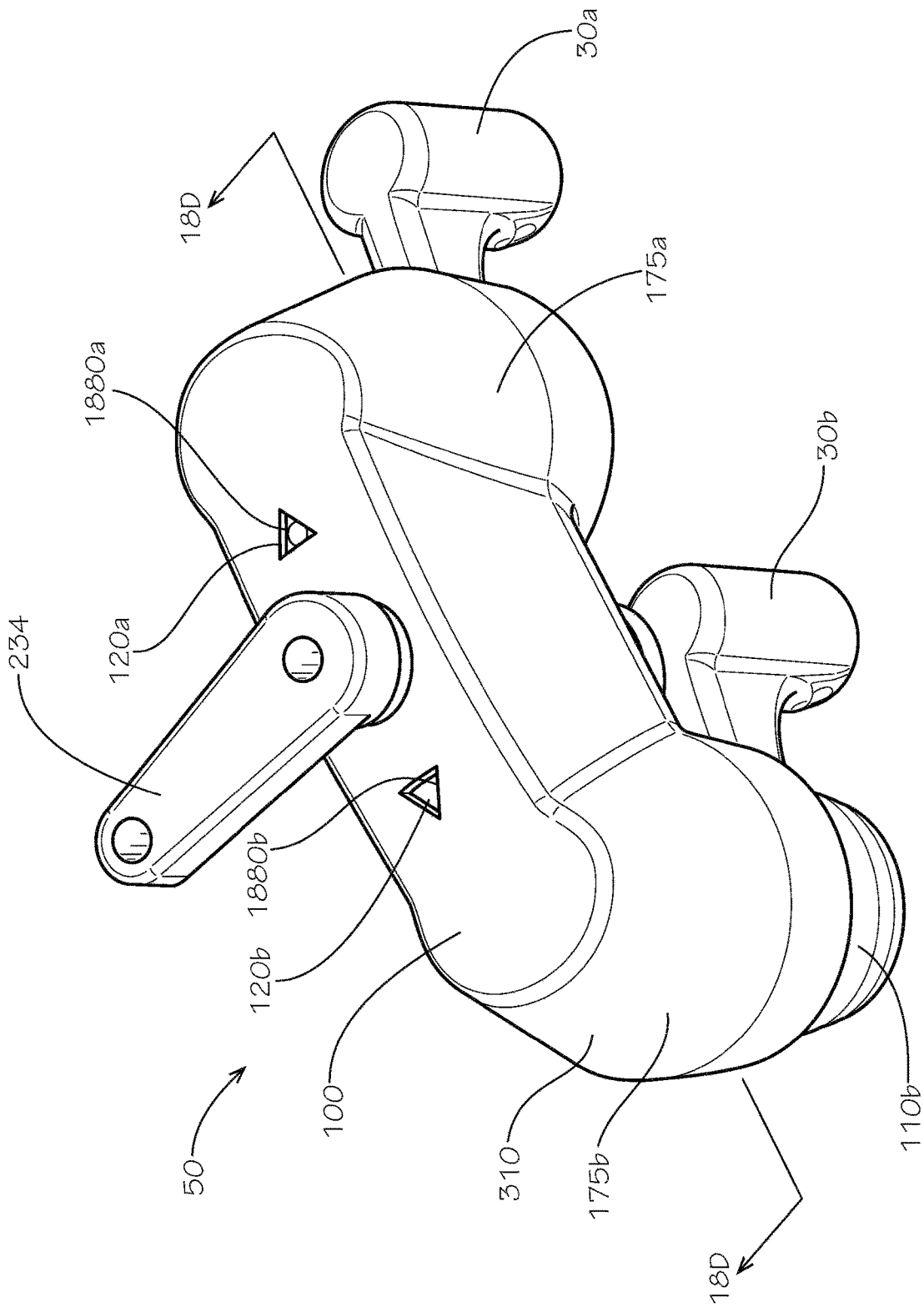
FIG. 18A is a top perspective view of a transfer device together with a receiver of a first support platform and a receiver of a second support platform in accordance with another aspect of the current disclosure, the transfer device comprising a set of indicators in accordance with another aspect of the current disclosure and with the set of indicators in a first indicating condition showing the receiver of the first support platform lockably engaged with the first docking cup of the transfer device.

FIGS. 18A-18D show the transfer device 100 together with the receiver 110a (shown in FIG. 1) of the first support platform 30a and the receiver 110b of the second support platform 30b in accordance with another aspect of the current disclosure, the transfer device 100 comprising a set of indicators 120a,b in accordance with another aspect of the current disclosure. FIG. 18A specifically shows a top perspective view of the transfer device 100 with the set of indicators 120a,b in a first indicating condition showing the receiver 110a of the first support platform 30a lockably engaged with the first docking cup 175a of the transfer device. As shown, each of the indicators 120a,b can be positioned inside the housing 310 and can be only partially visible from outside the transfer device 100.

Figure 18B:
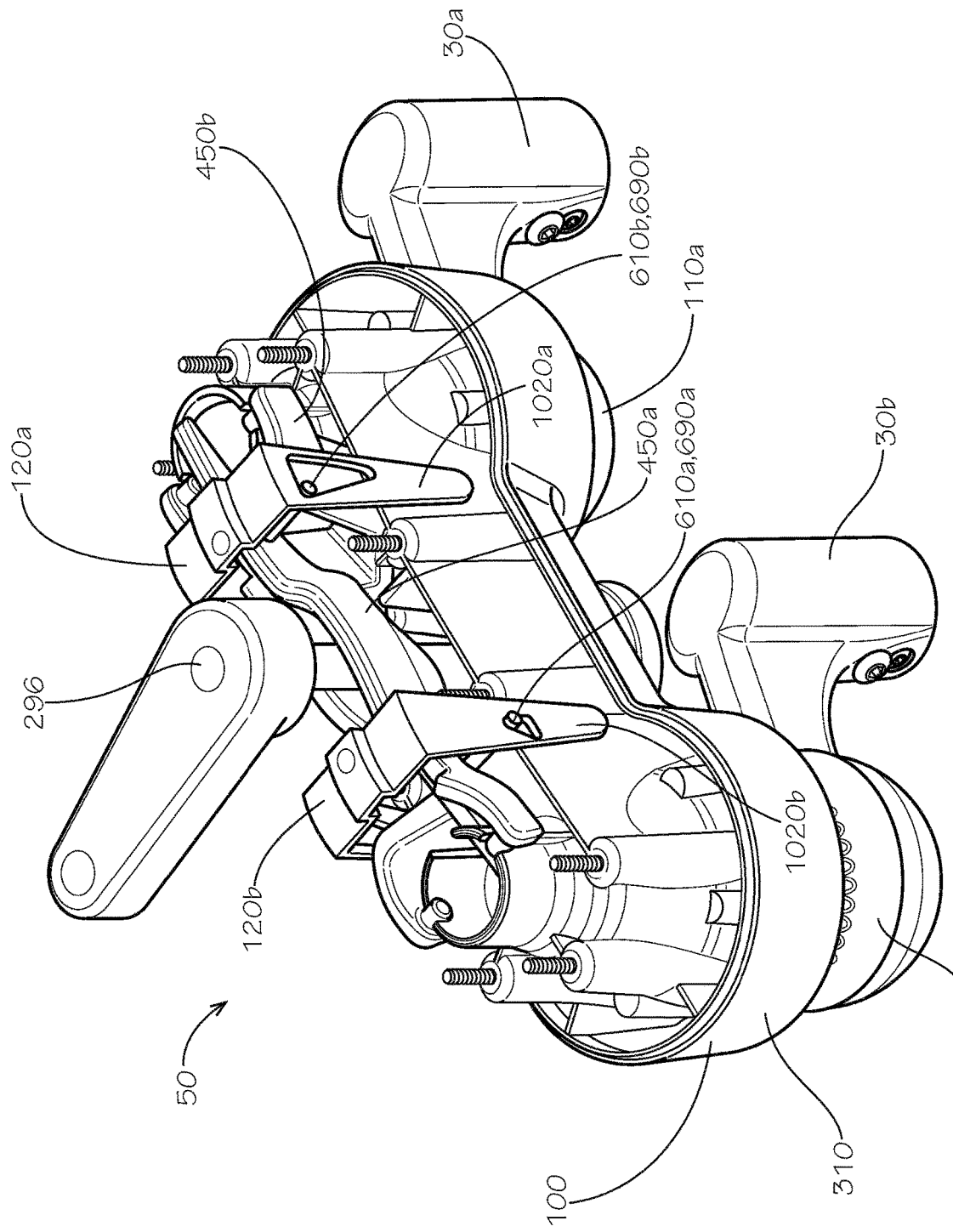
FIG. 18B is a top perspective view of the transfer device and the receivers of FIG. 18A with a portion of the housing of the transfer device removed.
Figure 18C:
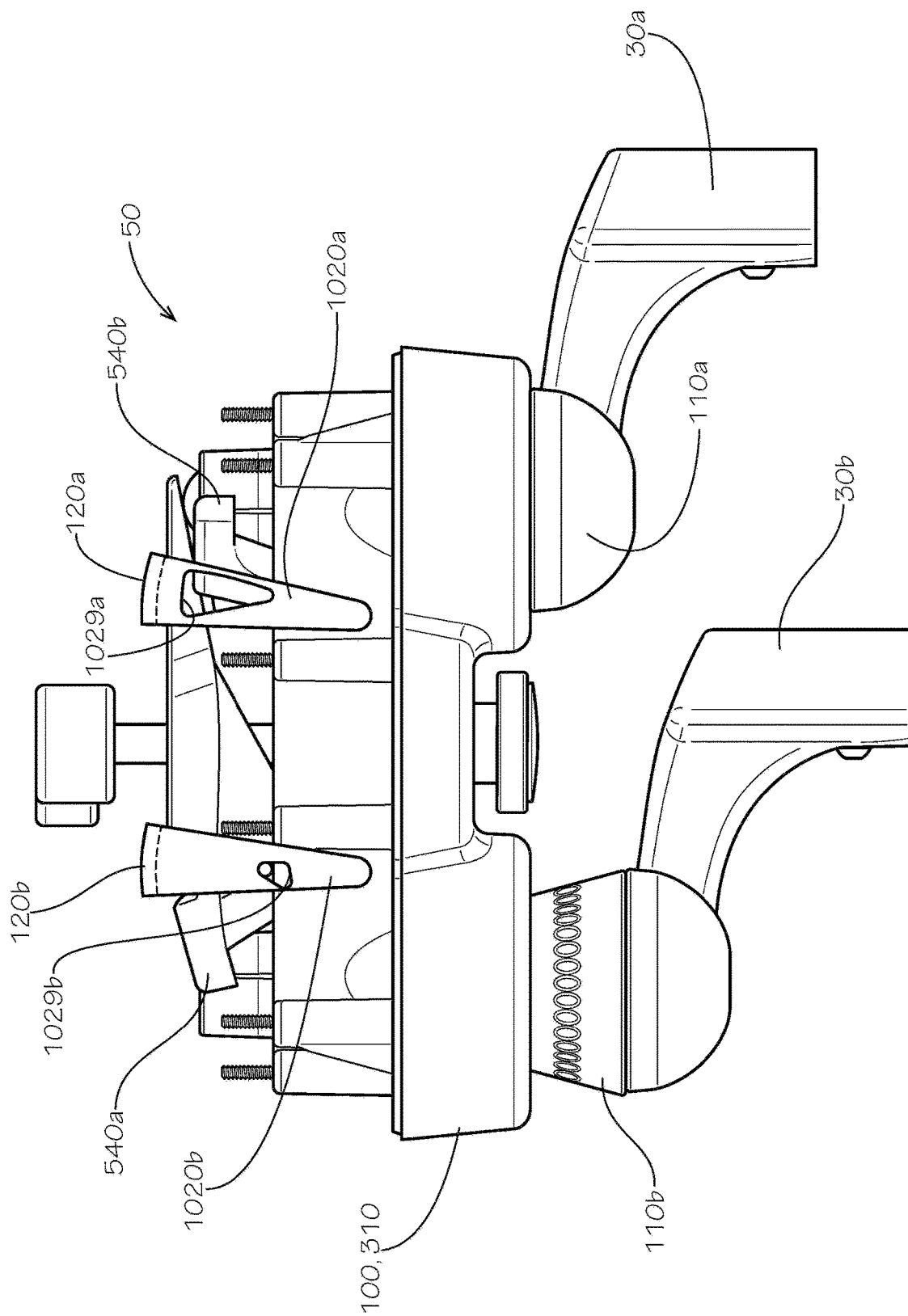
FIG. 18C is a front view of the transfer device and the receivers of FIG. 18A with the portion of the housing of the transfer device removed.

FIG. 18B shows a top perspective view and FIG. 18C shows a front view of the transfer device 100 and the receivers 110a,b with a portion of the housing 310 of the transfer device 100 removed. As the pins 690a,b move and, as shown, rotate from one indicating condition to another indicating condition due to movement of the security levers 450a,b, the movement and thereby indication of movement and engagement to the user is visible through a respective window 1880a,b (shown in FIG. 18A) defined in the housing 310. Each of the indicators 120a,b can be biased towards one position—for example, in or out with respect to a center of the transfer device 100—with a biasing element (not shown). Each of the indicators 120a,b can define a mark on a surface such as a top surface. In some aspects, as shown, the mark can be a circular mark and can indicate engagement or disengagement of a corresponding receiver 110a,b such as the receiver 110a,b on the same side of the transfer device 100 as the indicator 120a,b. As shown, in some aspects, the pivot links 1020a,b can be formed monolithically with the indicator 120a,b, and each of the pivot links 1020a,b can define a unique pivot slot 1029a,b for translating rotational movement of the pin 690a,b about one axis—here, the pivot portion 540a,b—into rotational movement of the indicator 120 about another axis. In some aspects, each of the windows 1880a,b can comprise a barrier allowing visibility to the indicators 120a,b but also preventing soiling of the indicators 120a,b due to liquids and/or other materials entering the transfer device 100.

Figure 18D:
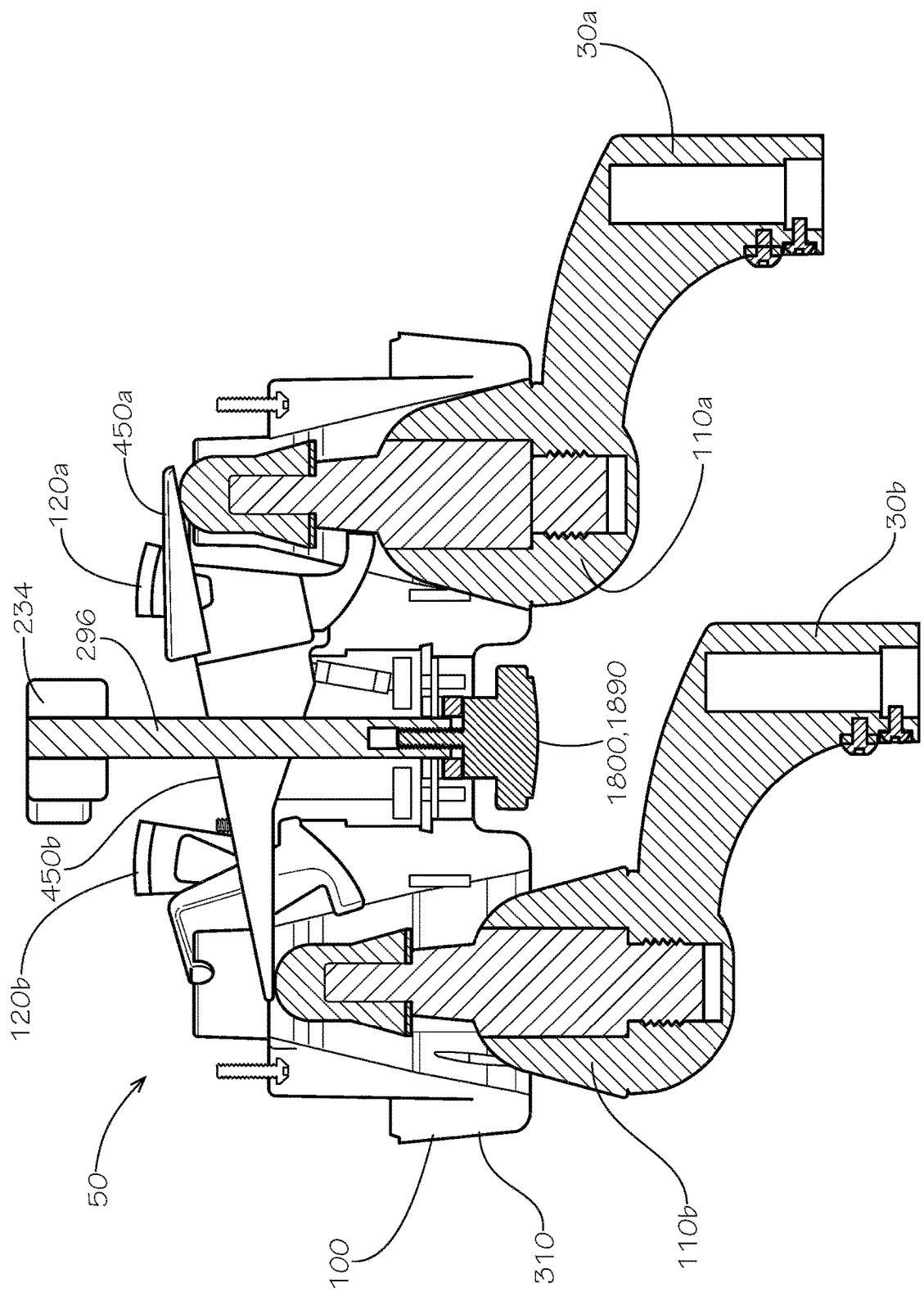
FIG. 18D is a front sectional view of the transfer device and the receivers of FIG. 18A with the portion of the housing of the transfer device removed and taken along line 18D-18D of FIG. 18A.

FIG. 18D shows a front sectional view of the transfer device 100 and the receivers 110a,b with the portion of the housing 310 of the transfer device 100 removed and taken along line 18D-18D of FIG. 18A. As shown, a brake mechanism 1800 can, when tightened, be used to prevent rotation of the arm 234 and any structure supported thereby with respect to the transfer device 100. The brake mechanism 1800 can comprise a brake fastener 1890, which can be fastened to the support post 296, and washers positioned therebetween to fix a rotational position of the brake fastener 1890 with respect to the support post 296 and the transfer device 100. As shown, the brake mechanism 1800 and the support post 296 can be positioned in close proximity to and in a space between the security levers 450a,b and the indicators 120a,b without interfering with their operation.

Operation of each of the indicator linkages 610a,b (shown in FIG. 18B) and the security mechanism 410 can be automatic as disclosed herein. In some aspects, as shown, any of the indicators 120, including the indicators 120a,b, can comprise a pointer or bar. In other aspects, any indicators 120 can comprise a flag, which can define any geometry. In other aspects, any indicators 120 can comprise a colored surface exposed through an opening in the housing. Any of the indicator 120 can be positioned on a face, a side (including at or through a seam of the housing 310), a top, or a bottom of the housing 310. In some aspects, any of the indicators 120 can positively indicate both engaged, locked, or latched and disengaged, unlocked, or unlatched positions. In other aspects, any of the indicators 120 can positively indicate only the engaged or the disengaged positions but not both. Indication can be by color (for example, red vs. green), by alignment vs. misalignment, by a pictorial image such as that of the aforementioned padlock, or by any other desirable means.

Figure 19A:
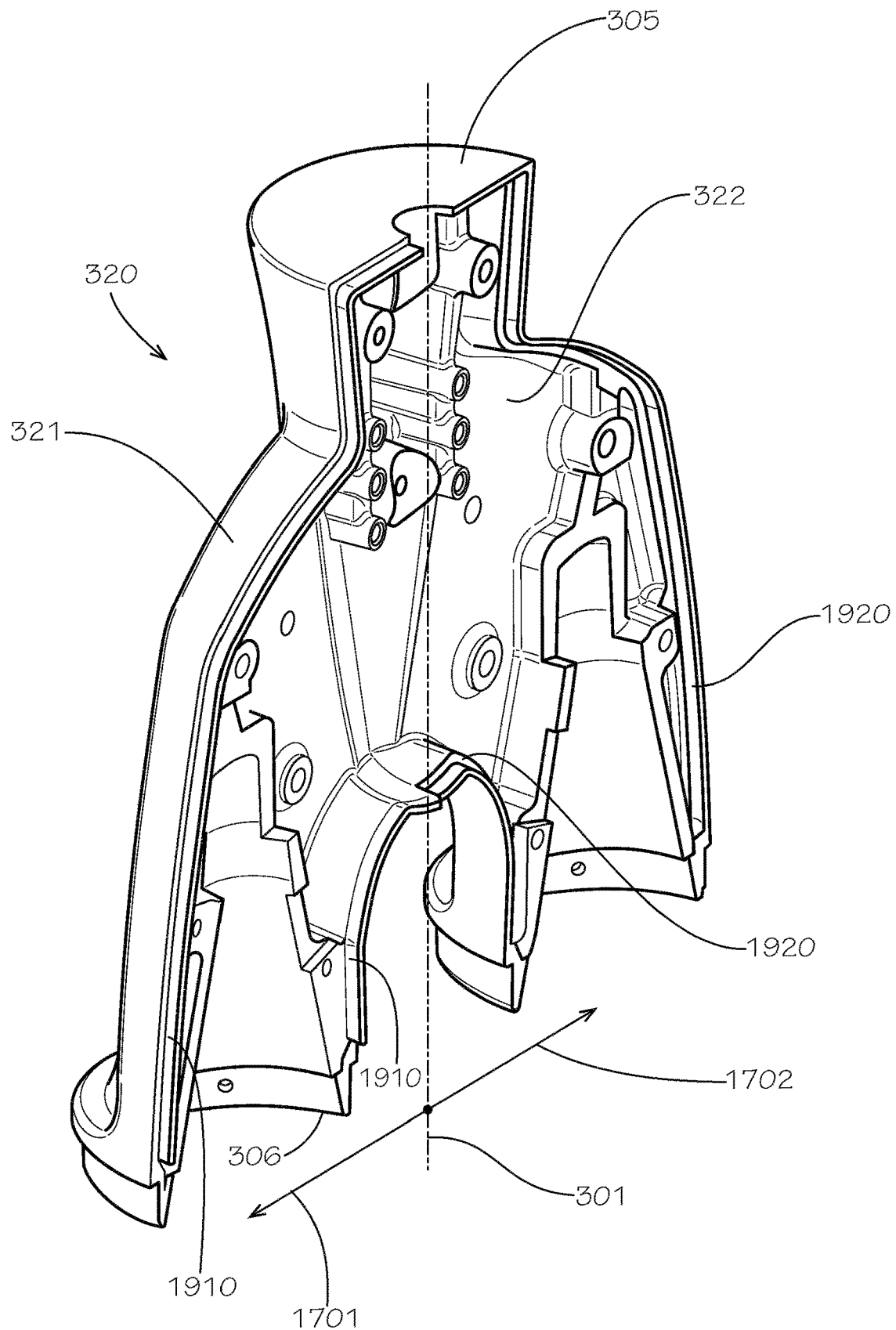
FIG. 19A is a perspective view of a housing of the transfer device of FIG. 1 in accordance with another aspect of the current disclosure.
Figure 19B:
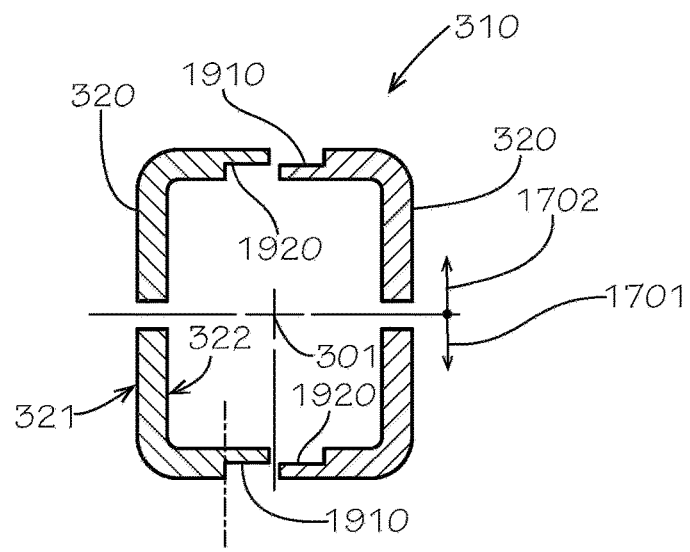
FIG. 19B is a sectional view of the housing of FIG. 19 in accordance with another, more simplified aspect of the current disclosure.
Figure 19C:
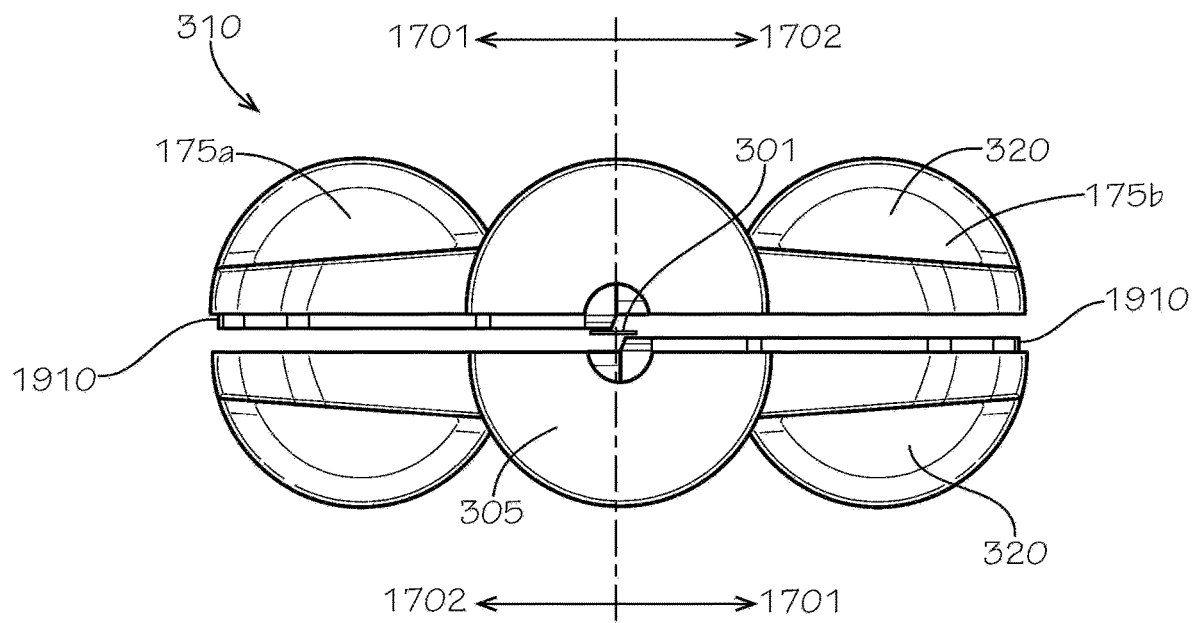
FIG. 19C is a top view of the housing of FIG. 19 in close proximity to a mating housing having identical geometry.

FIGS. 19A-19C show a perspective view of the housing 310 of the transfer device 100 (shown in FIG. 3) in accordance with another aspect of the current disclosure. FIG. 19A specifically shows a perspective view of the housing 310 (shown in FIG. 3) of the transfer device 100. As shown, two identical instances of a housing half 320 can be configured to form the housing 310. The housing half 320 can comprise a raised edge or flange 1910 on any exterior edges of a first side 1701 and a pocket or recess 1920 on any exterior edges of a second side 1702, where the first side 1701 and the second side 1702 can be separated by the axis 301. In some aspects, as shown, either of the flange 1910 and the recess 1920 can be continuous from a first end of the respective flange 1910 or recess 1920 to a second end of the respective flange 1910 or recess 1920. In other aspects, each of the flange 1910 and the recess 1920 can be broken or interrupted or alternate between a flange and a recess features while optionally still presenting a coplanar seam in the housing 310 as assembled. As shown, an exterior surface 321 and an interior surface 322 can be as described above with respect to the exterior surfaces 321a,b and the interior surfaces 322a, b.

FIG. 19B shows a sectional view, and FIG. 19C shows a top view of the housing 310 in close proximity to a mating housing 310 having or defining identical geometry. In contrast to the housing half 320 in FIG. 19A presenting a coplanar seam on both sides 1701,1702 of the housing half 320, as shown in FIG. 19C the seams on opposite sides 1701,1702 can be offset from one other and offset from the axis 301 when the housing 310 is assembled. Also as shown, the flange 1910 of the first housing half 320 can nest within the recess 1920 of the second housing half 320 and vice versa. An edge of each of the flange 1910 and the recess 1920 can be slightly relieved to along either the entire length or at certain points such as the transition between the first side 1701 and the second side 1702 to facilitate smooth assembly between parts by simple insertion of the first housing half 320 into the second housing half 320 by translation of the first housing half 320 with respect to the second housing half 320.

The components of the transfer system 50 (shown in FIG. 1) and, more specifically, the transfer device 100 and any portion thereof can be formed from any one of a variety of materials selected based on their strength characteristics, weight, and cost. In some aspects, it will be beneficial to select a material with sufficient strength to avoid deformation, corrosion, or fatigue in use. In some aspects, the housing 310 can be formed from a material such as aluminum, which can be cast, molded, and/or machined to produce any of the features disclosed herein. In some aspects, the security mechanism 410 or portions thereof can be formed from a stainless steel material such as, for example and without limitation, grade 304 or equivalent. In other aspects, another material can be used for any of the parts such as, for example and without limitation, a metal other than stainless steel, a composite material, or a polymer resin—including of the fiber-reinforced kind. In some aspects, as shown, the security mechanism 410 (shown in FIG. 6) or portions thereof can be formed from sheet metal through traditional sheet metal forming processes. In other aspects, the structure can be formed from a powder in a 3D printing process, from pellets in a molding process, or from another raw material form and forming process. In some aspects, components such as the biasing members 570a,b (shown in FIG. 5) can be configured and selected to deform, in which case a material with appropriate characteristics such as, for example and without limitation, spring steel can be used. In other aspects, another material can be used for the parts configured to deform such as, for example and without limitation, a metal other than spring steel or a rubber-like flexible material.

Figure 20A:
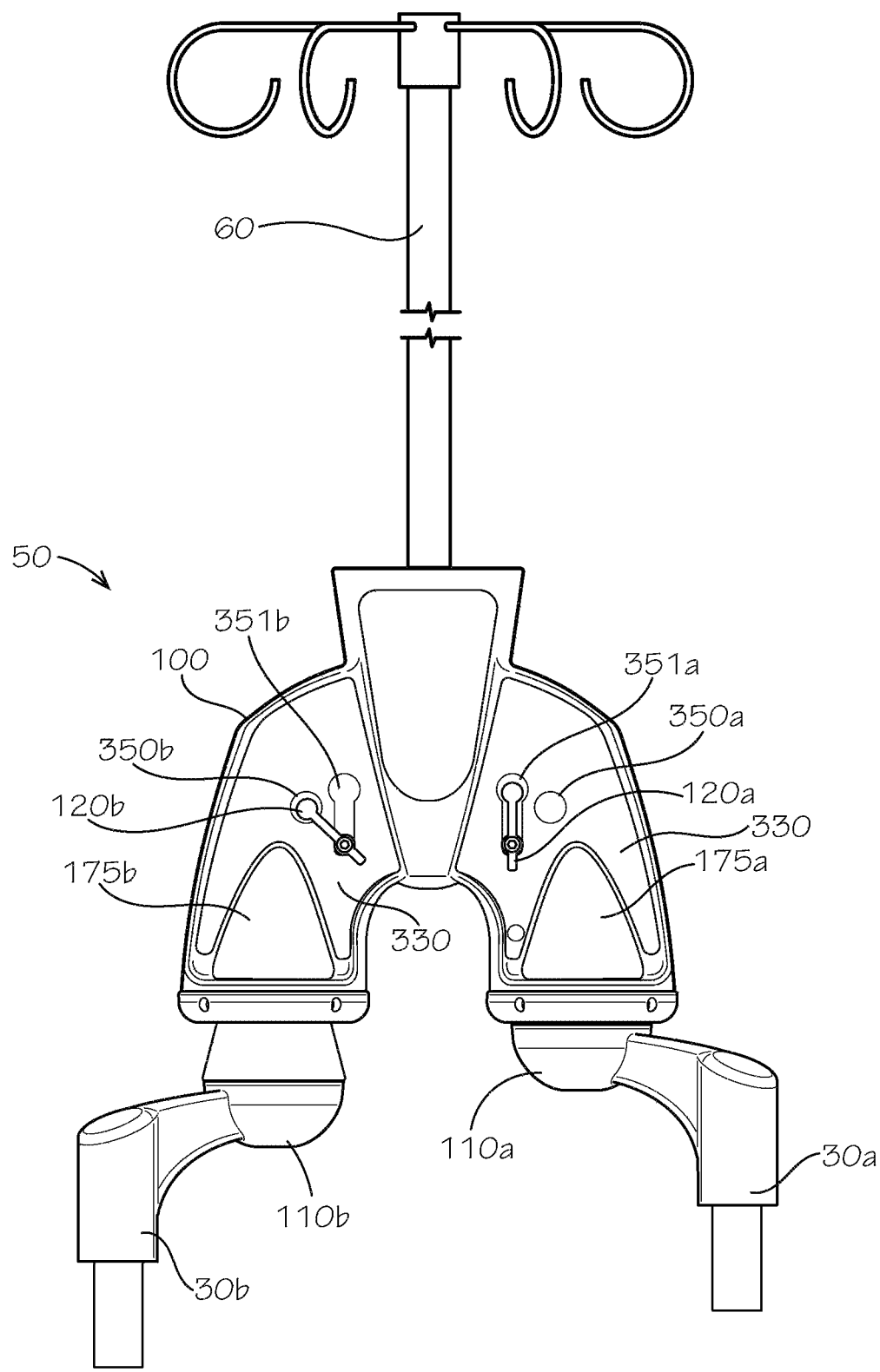
FIG. 20A is a front view of the transfer device of FIG. 1 together with a receiver of the first support platform, a receiver of the second support platform, and a patient care apparatus supported by the transfer device, with the set of indicators of the transfer device in a first indicating condition showing the receiver of the first support platform lockably engaged with the first docking cup of the transfer device.
Figure 20B:
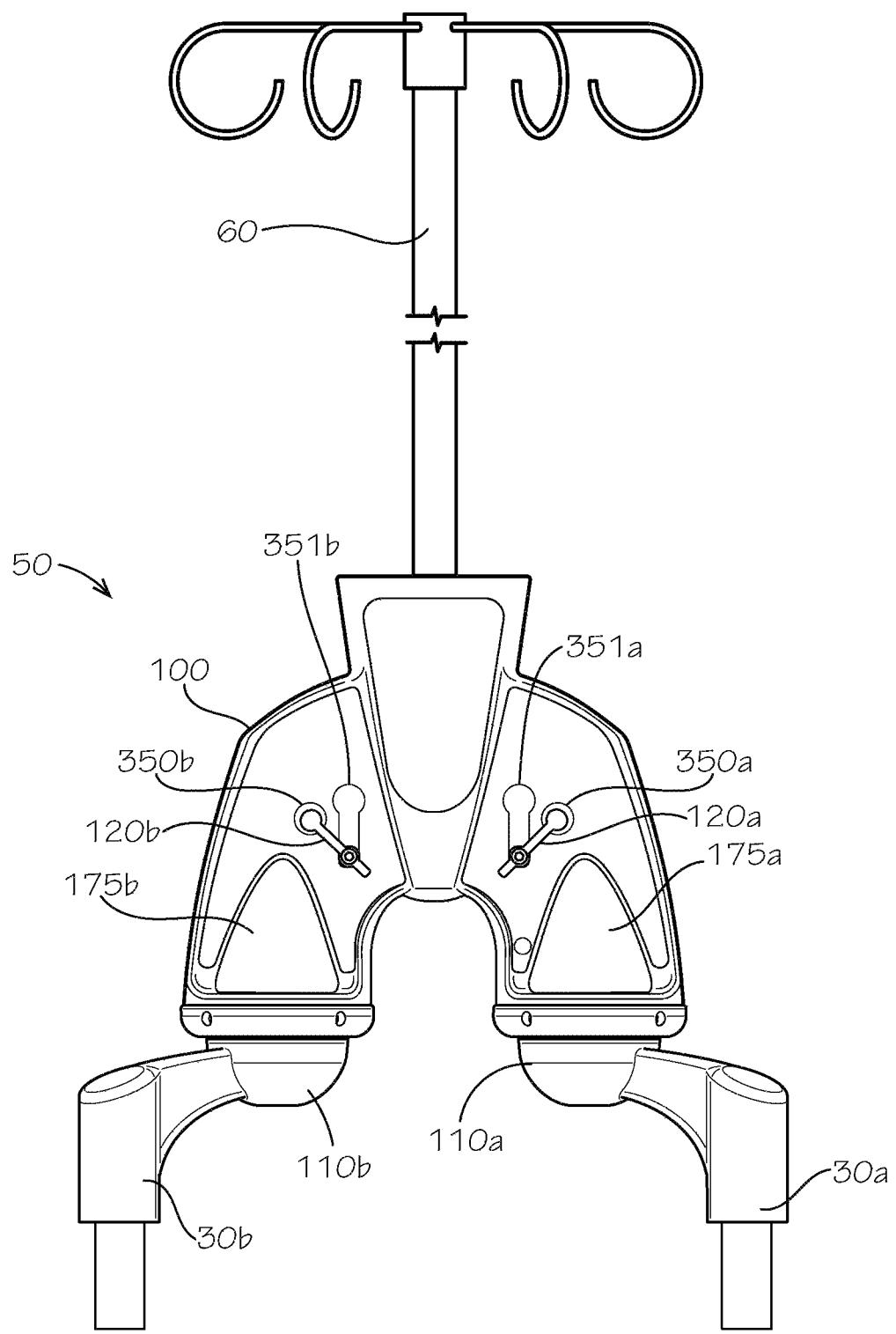
FIG. 20B is a front view of the transfer device, the receivers, and the patient care apparatus of FIG. 20A with the set of indicators in a second indicating condition showing the respective receivers of the first support platform and the second support platform inserted into but not lockably engaged with each of the first docking cup and the second docking cup of the transfer device.
Figure 20C:
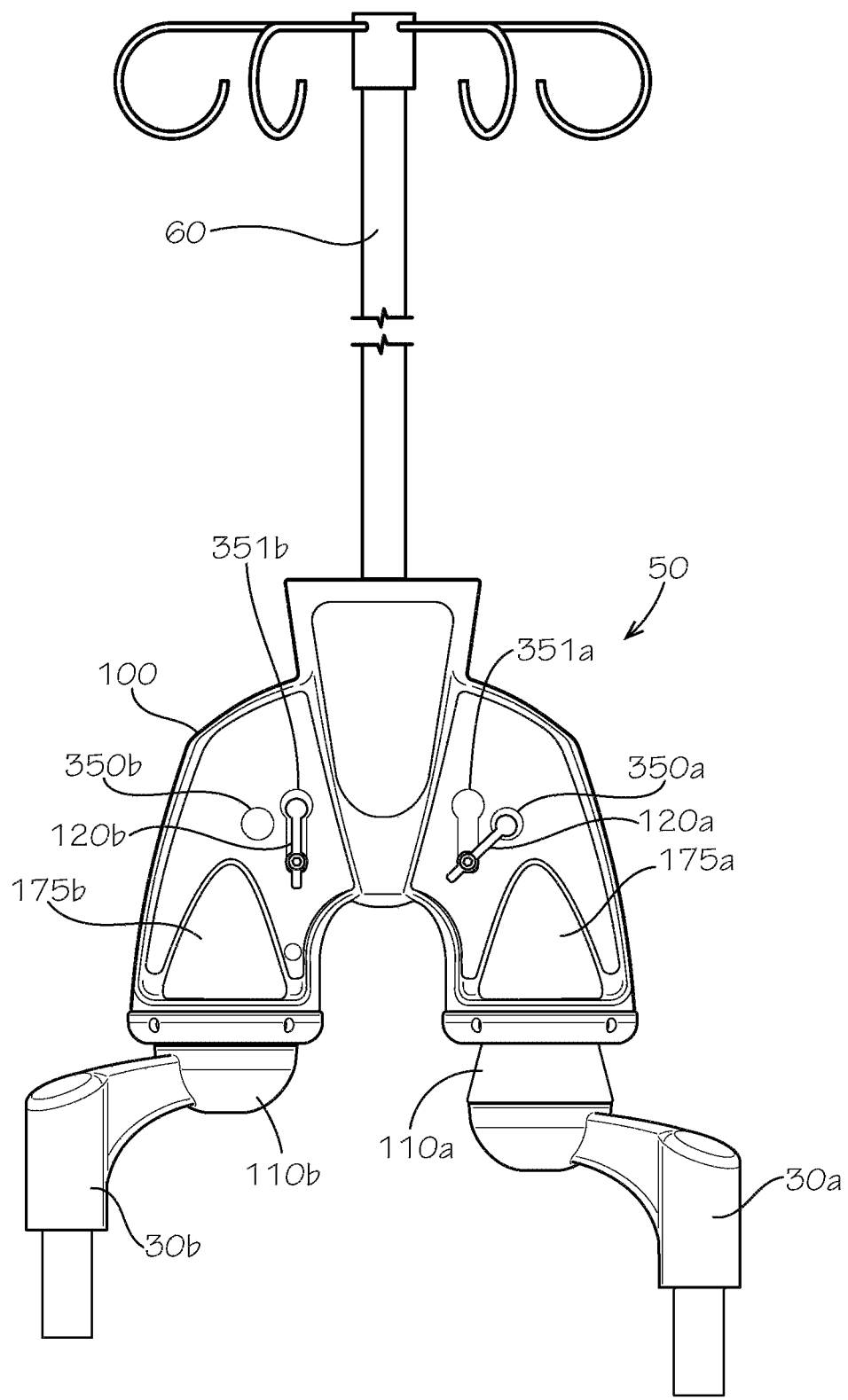
FIG. 20C is a front view of the transfer device, the receivers, and the patient care apparatus of FIG. 20A with the set of indicators in a third indicating condition showing the receiver of the second support platform lockably engaged with the second docking cup of the transfer device.

FIGS. 20A-20C show front views of the transfer device 100 of FIG. 1 together with the receiver 110a of the first support platform 30a, the receiver 110b of the second support platform 30b, and the patient care apparatus 60 supported by the transfer device 100 in various indicating conditions. FIG. 20A specifically shows the transfer device 100 with the set of indicators 120a,b of the transfer device 100 in a first indicating condition showing the receiver 110*a* of the first support platform 30*a* lockably engaged with the first docking cup 175*a* but not the second docking cup 175*b* of the transfer device 100. As shown, a position of the indicator 120*b* over the mark 350*b*, which can be colored or otherwise configured to indicate disengagement (such as with the color red), can indicate to the user that the transfer device 100 is not lockably engaged or latched to the receiver 110*b*, while a position of the indicator 120*a* over the mark 351*a*, which can be colored or otherwise configured to indicate engagement (such as with the color green), can indicate to the user that the transfer device 100 is still lockably engaged or latched to the receiver 110*a*.

FIG. 20B shows the transfer device 100 with the set of indicators 120*a,b* in a second indicating condition showing the receiver 110*a* of the first support platform 30*a* engaged with the first docking cup 175*a* and the receiver 110*b* of the second support platform 30*b* engaged with the second docking cup 175*b* of the transfer device 100. As shown, a position of the indicator 120*b* over the mark 350*b* and a position of the indicator 120*a* over the mark 350*a*, each of which can be colored or otherwise configured to indicate disengagement (such as with the color red), can indicate to the user that the transfer device 100 is not lockably engaged or latched to either of the receivers 110*a,b*.

FIG. 20C shows a front view of the transfer device 100, receivers 110*a,b*, and the patient care apparatus 60 with the set of indicators 120*a,b* in a third indicating condition showing the receiver 110*b* of the second support platform 30*b* lockably engaged with the second docking cup 175*b* but not the first docking cup 175*a* of the transfer device 100. As shown, a position of the indicator 120*a* over the mark 350*a*, which can be colored or otherwise configured to indicate disengagement (such as with the color red), can indicate to the user that the transfer device 100 is not lockably engaged or latched to the receiver 110*a*, while a position of the indicator 120*b* over the mark 351*b*, which can be colored or otherwise configured to indicate engagement (such as with the color green), can indicate to the user that the transfer device 100 is still lockably engaged or latched to the receiver 110*b*.

A method of using the transfer system 50 (shown in FIG. 1) can comprise lockably engaging the transfer device 100 of the transfer system 50 with one of the receivers 110*a,b* (shown in FIG. 1) of the transfer system 50, the transfer device comprising the housing 310 (shown in FIG. 3) comprising the first docking cup 175*a* and the second docking cup 175*b*, the security mechanism 410 (shown in FIG. 6) positioned inside the housing 310, and a pair of the indicators 120*a,b*, which can be coupled to the security mechanism 410 and at least partially visible from outside the housing 310. The method can further comprise positioning a first indicator 120*a,b* of the pair of indicators 120*a,b* in a first indicating position with respect to the housing 310, the first indicating position indicating to a user of the transfer system 100 that the receiver has been lockably engaged with the one of the first docking cup 175*a* and the second docking cup 175*b*.

The method can further comprise aligning the first indicator 120*a* of the pair of indicators 120*a,b* with a first mark 350*a* (for example and without limitation, as any other mark or mark position, orientation, or design can be used) on the housing 310, the first mark 350*a* indicating to the user of the transfer system 50 that the receiver 110*a* of the transfer system 50 has been lockably engaged with the one of the first docking cup 175*a* and the second docking cup 175*b*. As shown in the aforementioned FIGS. 20A-20C, lockably engaging the transfer device 100 can comprise lockably engaging the one of the receivers 110*a,b* with one of the first docking cup 175*a* and the second docking cup 175*b*. As described above, either of the positioning and aligning steps can be performed automatically by the transfer device 100 upon lockable engagement of the receiver 110*a,b* into the one of the first docking cup 175*a* and the second docking cup 175*b*. The method can comprise moving either of the indicators 120*a,b* with a pin 690*a,b* secured to the security lever 450*a,b* of the security mechanism 410. In some aspects, as shown in FIGS. 17A-17E, the method can comprise interfering with disengagement of the receiver 110*a,b* from the corresponding one of the first docking cup 175*a* and the second docking cup 175*b* when the corresponding indicator 120*a,b* is engaged.

Before transporting a patient from a room to another location, in reference again to FIG. 1 and FIGS. 20A-20C, the first docking cup 175*a* of the transfer device 100 can be docked with, and secured to, the support platform 30*a*. In preparation for patient transport, the transfer device 100 can be repositioned so that the second docking cup 175*b* faces the patient bed 40, and the patient bed 40 can be moved closer to the support platform 30*a*. Activation of the lift mechanism 43 can lower the height 48 of the mattress 42 sufficiently to permit the receiver 110*b* of the support platform 30*b* to be maneuvered directly underneath, and into generally coaxial alignment with, the second docking cup 175*b* of the transfer device 100. Further activation of the lift mechanism 43 of the patient bed 40 can raise the mattress 42 and also raise the receiver 110*b* of the support platform 30*b*, causing it to dock with the transfer device 100. As shown in FIG. 20B, the receiver 110*a* attached to the support platform 30*a* and the receiver 110*b* attached to the support platform 30*b* can be simultaneously engaged in their respective docking cups 175*a,b*. Under continued activation of the lift mechanism 43, which can cause the receiver 110*b* to lift the transfer device 100 away from the receiver 110*a*, the security mechanism 410 can automatically release the transfer device 100 from the receiver 110*a* and lock the transfer device 100 to the receiver 110*b*. The automatic release and engagement of the transfer device 100 during the transfer process can mean that the user of the transfer system 50 need not remember, much less properly perform, any manual latching or unlatching steps, which can simplify user training and enhance safety.

As shown in FIG. 20C, continued activation of lift mechanism 43 lifts the transfer device 100 out of engagement with the receiver 110*a* until the transfer device 100 clears the receiver 110*a*. As described above, various components of the transfer system 50 can form a system of pivoting linkages, which can permit caregivers to position the patient care apparatus 60 where it is needed for optimal patient care.

Moving the patient bed 40 away from the support platform 30*a* and out of docking alignment enables the user of the transfer system 50 to reverse the lift mechanism 43 to lower the mattress height 48 to a desired working height. Caregivers are now free to reposition the patient care apparatus 60 and the transfer device 100 so both nest closely to the patient bed 40 and the patient's head as may be desired without disturbing the connections between the patient and the patient care apparatus 60. Articulation of the transfer device 100 by, for example and without limitation, rotation of the arms 70 permits nursing staff to minimize a total footprint of (i.e., a required floor space for) the support platform 30*b* for efficient and safe transport, in tandem with the patient care apparatus 60, through doorways, corridors, elevators, and so forth.

One should note that conditional language, such as, among others, "can," "could," "might," or "may," unless specifically stated otherwise, or otherwise understood within the context as used, is generally intended to convey that certain aspects include, while other aspects do not include, certain features, elements and/or steps. Thus, such conditional language is not generally intended to imply that features, elements and/or steps are in any way required for one or more particular aspects or that one or more particular aspects necessarily comprise logic for deciding, with or without user input or prompting, whether these features, elements and/or steps are included or are to be performed in any particular aspect.

It should be emphasized that the above-described aspects are merely possible examples of implementations, merely set forth for a clear understanding of the principles of the present disclosure. Any process descriptions or blocks in flow diagrams should be understood as representing modules, segments, or portions of code which comprise one or more executable instructions for implementing specific logical functions or steps in the process, and alternate implementations are included in which functions may not be included or executed at all, may be executed out of order from that shown or discussed, including substantially concurrently or in reverse order, depending on the functionality involved, as would be understood by those reasonably skilled in the art of the present disclosure. Many variations and modifications may be made to the above-described aspect(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

That which is claimed is:

1. A transfer system comprising:
   a receiver; and
   a transfer device comprising:
      a housing comprising a first docking cup and a second docking cup, each of the first docking cup and the second docking cup configured to receive and lockably engage the receiver;
      a security mechanism positioned inside the housing and configured to engage with the receiver through either of the first docking cup and the second docking cup; and
      a pair of indicators coupled to the security mechanism and at least partially visible from outside the housing, each of the pair of indicators configured to indicate to a user of the transfer system that the receiver has been lockably engaged with one of the first docking cup and the second docking cup.

2. The system of claim 1, wherein the security mechanism comprises:
   a first security lever;
   a first biasing member engaged with the first security lever and configured to bias the first security lever towards engagement with the receiver;
   a second security lever; and
   a second biasing member engaged with the second security lever and configured to bias the second security lever towards engagement with the receiver.

3. The system of claim 2, further comprising a support post configured to support a patient care apparatus, the support post positioned between the first security lever and the second security lever.

4. The system of claim 2, wherein a thickness of each of the first security lever and the second security lever is substantially constant.

5. The system of claim 1, wherein the pair of indicators is a first pair of indicators, the transfer device further comprising a second pair of indicators positioned on a side of the transfer device that is opposite from a side of the transfer device on which the first pair of indicators is positioned.

6. The system of claim 5, wherein a first indicator of the first pair of indicators is fixably joined to a first indicator of the second pair of indicators via an indicator linkage.

7. The system of claim 6, wherein the pair of indicators are fixably joined to each other via a pivot shaft of the indicator linkage and configured to move in unison.

8. A transfer device comprising:
   a housing comprising a first docking cup and a second docking cup, each of the first docking cup and the second docking cup configured to receive and lockably engage a receiver of a transfer system;
   a security mechanism positioned inside the housing; and
   a pair of indicators coupled to the security mechanism and at least partially visible from outside the housing, each of the pair of indicators configured to indicate to a user of the transfer system that the receiver has been lockably engaged with one of the first docking cup and the second docking cup.

9. The device of claim 8, wherein the housing comprises a pair of housing halves defining identical geometry.

10. The device of claim 8, wherein each of the pair of indicators comprises a mounting hub and a first portion extending radially outward from the mounting hub.

11. The device of claim 8, wherein each of the pair of indicators defines a weakened area, each indicator of the pair of indicators configured to deform first at the weakened area upon contact with a load.

12. The device of claim 8, wherein at least a portion of each of the pair of indicators is positioned outside the housing.

13. The device of claim 8, wherein each of the pair of indicators is positioned inside the housing but visible from outside the housing.

14. The device of claim 8, wherein each of the pair of indicators extends from or is visible from one of an upward facing surface and a side facing surface of the housing.

15. The device of claim 8, wherein the housing defines at least one mark for each of the pair of indicators, the mark indicating one of engagement and disengagement of the security mechanism with the receiver.

16. A method of using a transfer system, the method comprising:
   lockably engaging a transfer device of the transfer system with a receiver of the transfer system, the transfer device comprising:
      a housing comprising a first docking cup and a second docking cup, lockably engaging the transfer device comprising lockably engaging the receiver with one of the first docking cup and the second docking cup;
      a security mechanism positioned inside the housing; and
      a pair of indicators coupled to the security mechanism and at least partially visible from outside the housing; and positioning a first indicator of the pair of indicators in a first indicating position with respect to the housing, the first indicating position indicating to a user of the transfer system that the receiver has been lockably engaged with the one of the first docking cup and the second docking cup.

17. The method of claim 16, further comprising aligning a first indicator of the pair of indicators with a first mark on the housing.

18. The method of claim 16, wherein the positioning step is performed automatically by the transfer device upon lockable engagement of the receiver into the one of the first docking cup and the second docking cup.

19. The method of claim 16, further comprising moving the first indicator with a pin secured to a security lever of the security mechanism.

20. The method of claim 16, further comprising interfering with disengagement of a receiver of the transfer system from the corresponding one of the first docking cup and the second docking cup when the first indicator is engaged.

* * * * *